US008682590B2

(12) United States Patent
Fortmann et al.

(10) Patent No.: US 8,682,590 B2
(45) Date of Patent: Mar. 25, 2014

(54) METHOD FOR DETERMINING AN EQUILIBRIUM STRUCTURE OF A PROTEIN IN A PREDETERMINED ENVIRONMENT

(75) Inventors: Charles Michael Fortmann, Bellport, NY (US); Yeona Kang, Port Jefferson, NY (US)

(73) Assignee: The Research Foundation of State University of New York, Stony Brook, NY (US)

( * ) Notice: Subject to any disclaimer, the term of this patent is extended or adjusted under 35 U.S.C. 154(b) by 848 days.

(21) Appl. No.: 12/301,957

(22) PCT Filed: Apr. 27, 2007

(86) PCT No.: PCT/US2007/067639
§ 371 (c)(1),
(2), (4) Date: Jun. 22, 2010

(87) PCT Pub. No.: WO2007/140061
PCT Pub. Date: Dec. 6, 2007

(65) Prior Publication Data
US 2010/0280223 A1    Nov. 4, 2010

Related U.S. Application Data

(60) Provisional application No. 60/808,167, filed on May 23, 2006.

(51) Int. Cl.
*G06F 19/00* (2011.01)
*G06F 17/18* (2006.01)

(52) U.S. Cl.
USPC ............................................. 702/19; 530/350

(58) Field of Classification Search
USPC ......................................................... 702/19
See application file for complete search history.

(56) References Cited

U.S. PATENT DOCUMENTS

| 5,241,470 | A  | * | 8/1993  | Lee et al. ........................ 436/86 |
| 6,684,162 | B2 | * | 1/2004  | Parris et al. ..................... 702/27 |
| 2007/0122864 | A1 |  | 5/2007  | Woods et al. |
| 2010/0304983 | A1 |  | 12/2010 | Fortmann et al. |

OTHER PUBLICATIONS

Erman et al., "Equilibrium states of rigid bodies with multiple interaction sites: Application to protein helices", 1997, Journal of Chemical Physics, vol. 107, No. 6, pp. 2046-2060.*
Karplus et al., "The internal dynamics of globular proteins", 1981, Critical Reviews in Biochemistry and Molecular Biology, vol. 9, No. 4, pp. 293-349.*
Makowska et al., "Polyproline II conformation is one of many local conformational states and is not an overall conformation of unfolded peptides and proteins", 2006, Proceedings of the National Academy of Sciences, vol. 103, No. 6, pp. 1744-1749.*
Tappura, "Influence of Rotational Energy Barriers to the Conformational Search of Protein Loops in Molecular Dynamics and Ranking the Conformations", 2001, Proteins: Structure, Function, and Genetics, vol. 44, pp. 167-179.*
Kazerounian et al. Protofold: A Successive Kinetostatic Compliance Method for Protein Conformation Prediction. J. Mechanical Design, 2005, vol. 127, 4, pp. 712-717.*
Masek et al. J. Med. Chem. 1993,36, 1230-1238.*
U.S. Appl. No. 12/301,963, Oct. 17, 2012 Non-Final Office Action.
Avbejl, et al., "Prediction of the Three-Dimensional Structure of Proteins Using the Electrostatic Screening Model and Hierarchic Condensation", *Proteins: Structure, Function, and Genetics*, 31:74-96 (1998).
Dyson, et al., Database CapLus, DN 145:264901, "The Role of Hydrophobic Interactions in Initiation and Propagation of Protein Folding", *Proceedings of the National Academy of Sciences of the United States of America*, 103(35): 13057-13061 (2006).
Parker, et al., Database CapLus, DN 125-:108196 (Proteins: Structure, Function, and Genetics), 25(2):253-260 (1996).
Torrens, et al., Database CapLus, DN 148:185357, "Peptide Potential Energy Surfaces and Protein Folding", *Journal of the Argentine Chemical Society*, 94(1-3):27-47 (2006).
Wei, et al., "Molecular Dynamics Simulation of Folding of a Short Helical Peptide with Many Charged Residues", *J. Phys. Chem. B.*, 109:19980-19986 (2005).
U.S. Appl. No. 13/571,589, filed Aug. 10, 2012.
U.S. Appl. No. 12/301,963, Apr. 17, 2013 Response to Non-Final Office Action.

* cited by examiner

*Primary Examiner* — Michael Borin
(74) *Attorney, Agent, or Firm* — Baker Botts LLP

(57) ABSTRACT

Techniques for determining an equilibrium structure of a protein in a predetermined environment, the protein having Ramachandran angles and a known denatured structure, are disclosed. One example method includes determining a maximum RMS volume of the known denatured structure of the protein and calculating at least one force on the protein in its current structure in the predetermined environment. The net torque resulting from the at least one force for each of the Ramachandran angles of the protein is then determined. Then at least one section of the protein structure on a side of a Ramachandran angle with the greatest torque is rotated to form a new structure. A RMS volume for the new structure is then calculated, and the method is repeated using the new structure until the new RMS volume of the new protein structure is not less than the RMS volume of the starting structure.

11 Claims, 16 Drawing Sheets

Dark Red
Red
Orange
Yellow-Organge
Yellow
Yellow-Green
Light Green
Green
Blue-Green
Light Blue
Blue
Dark Blue

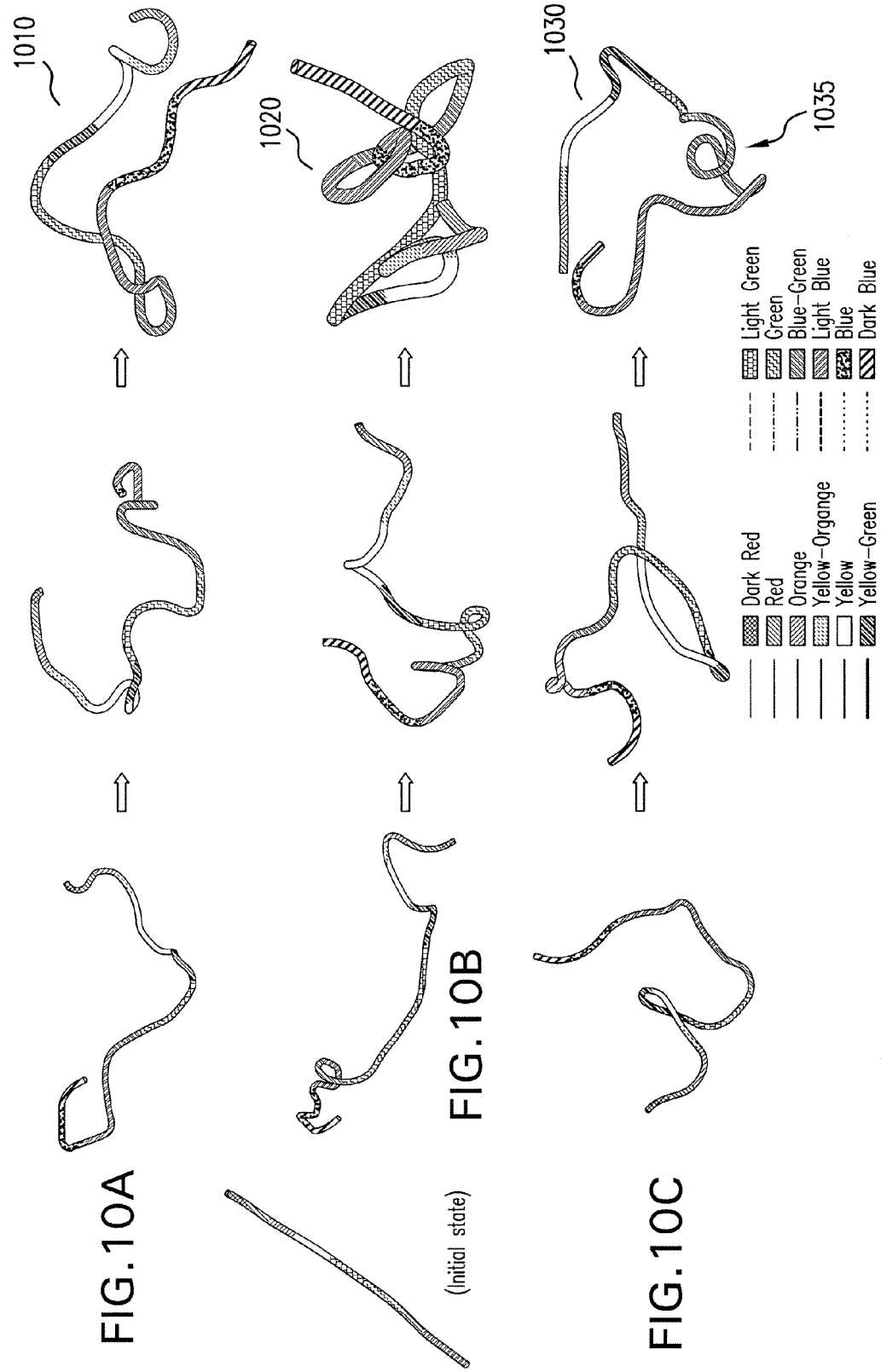

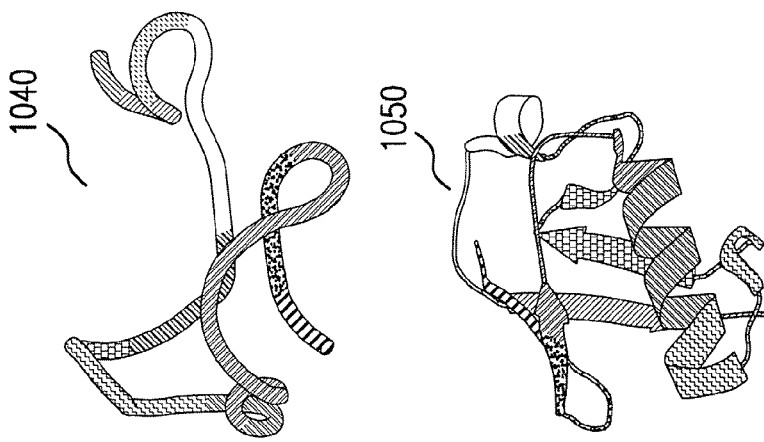
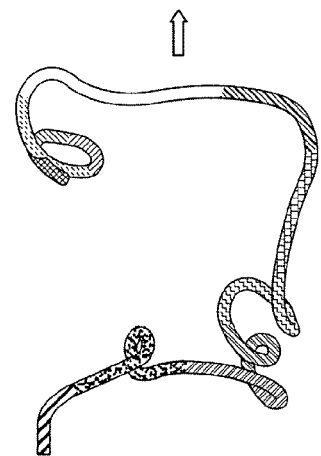
FIG.10E
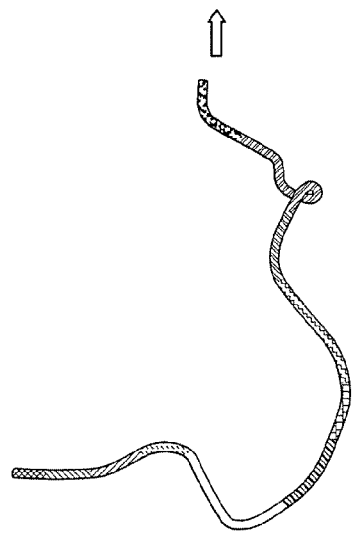
FIG.10D
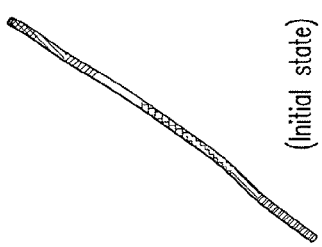

METHOD FOR DETERMINING AN EQUILIBRIUM STRUCTURE OF A PROTEIN IN A PREDETERMINED ENVIRONMENT

This application is a national phase of International Application PCT/US2007/067639, filed Apr. 27, 2007, which claims priority from U.S. Provisional Application No. 60/808,167 filed on May 23, 2006, entitled "Protein Autonomous Folding Units, Folding Dynamics and Structure," each of which are hereby incorporated by reference in their entirety.

A portion of the disclosure of this patent document contains material which is subject to copyright protection. The copyright owner has no objection to the facsimile reproduction by anyone of any portion of the patent document, as it appears in any patent granted from the present application or in the Patent and Trademark Office file or records available to the public, but otherwise reserves all copyright rights whatsoever.

BACKGROUND

The present invention relates to techniques for determining or predicting the secondary structure of a polypeptide, a protein, or an autonomous folding region thereof.

The secondary and higher-order structures of a protein dictate its function and biological activity, and are therefore critical to many fundamental life processes. Experimentally, such structures are often obtained through crystallography based on the assumption that the most stable conformation of a protein in solution is approximately the same as when it is crystallized. However, crystallography of a majority of proteins is currently unfeasible, presumably because chain flexibility and complex interactions existent within a protein molecule prevent it from forming crystals from solution.

Computational methods provide an alternative tool to explore protein structure, and are particularly valuable when a protein structures are inaccessible by crystallography or other experimental techniques. One computational approach to the determination of protein structure is based on energy minimization. The energy minimization approach, however, requires that the global (or molecular) free energy change to be mathematically describable in terms of local atomic bonding energies, and therefore cannot always provide an accurate description of the most stable protein secondary structure at the free energy minimum.

Furthermore, energy minimization methods do not address response speed and axis of rotation limitations, and as a result the models generate unrealistically-quick onsets of protein folding and/or volume change. Another approach, of which Molecular Dynamics is a typical example, employs explicit Newtonian motion functions to provide a time trajectory of a molecular system evolution. See Berendsen, H. J. C., Postma, J. P. M., van Gunsteren, W. F., DiNola, A., and Haak, J. R., J. Chem. Phys. 81, 8, 3684, (1984), and Karplus, Martin and McCammon, J. Andrew, Nat. Struc. Biol. 9, 9, 646 (2002).

This approach is severely limited by the small time steps needed to make it physically meaningful, as well as by the complex mathematical integration schemes needed to compute the motion functions. Therefore, it is best suited for exploration of molecular phenomena occurring over a short timeframe or for small size molecules, but is of little use for molecular phenomena occurring over a longer timeframe, such as protein folding. See Mirny, Leonid and Shakhnivich, Eugene, Annu. Rev. Biomol. Sturuct. 30, 361-96 (2001)).

Accordingly, there exists a need for a simulation method that incorporates the random forces imposed by the surrounding media and the relationship of their temporal dimension to the internal forces of a protein molecule, which method can significantly reduce the time required for a protein folding simulation, so that it becomes feasible for regular desktop computers to handle such a task.

SUMMARY

The present invention provides a means to determine or predict the secondary structure of a protein, a polypeptide, or an autonomous folding region thereof. This invention allows the computational time of a task as complex as protein folding simulation to be reduced to the order of minutes on regular desktop computers, as opposed to months on supercomputers typically required by other traditional simulation methods. This acceleration is made possible by a detailed analysis of the internal driving forces, the temporal interconnection between intramolecular forces and external random forces, and the corresponding computer codes that together describe and model the cooperative motion within a protein molecule that leads to protein folding.

Specifically, the present invention provides a method comprising (i) determining a mode of protein folding in which one part of a protein molecule moves relative to another part by a rotation around selected Ramachandran (dihedral) angles; (ii) determining the speed of protein folding in said mode under one or more internal force fields and external environmental factors such as temperature and solvent viscosity; and/or (iii) a computer code implementing such speed of motion to achieve the accelerated computation of protein folding.

The present invention has the following objectives:

To enable a physical analysis method and a computer source code that together provide a detailed description of protein and/or polypeptide and/or substructures or autonomous folding regions of a larger protein through a cooperative physical drift and diffusion model via dihedral angle change, wherein, in certain embodiments, said physical analysis method and said computer source code employ a constant mobility or an energy coupled mobility;

and/or wherein, in certain embodiments, said physical analysis method and computer source code determine a solvent induced displacement (diffusion) at one, many, or every time step iteration used by said analysis or in said computer source code;

and/or wherein, in certain embodiments, said physical analysis method and said computer source code use calculated electrostatic force as a function of local dielectric constants to calculate a motive force;

and/or wherein, in certain embodiments, said physical analysis method employs a physical representation of forces consistent with water surface tension and bubble envelope touching force conveyance;

and/or wherein, in certain embodiments, said computer source code represents said bubble envelope touching force conveyance as a distance-force map, for example, a square distance-force map;

and/or wherein, in certain embodiments, said physical analysis method is based upon an extension of the hydrophobic interaction between two hydrophobic amino acid residues to a longer distance based upon the density and size of the equilibrium bubble concentration found in the solvent;

and/or wherein, in certain embodiments, said computer source code addresses said physical hydrophobic force extension by a two-tier square well force map and/or a multi-tier series of square-well force maps, or other approximation of said bubble extension of said hydrophobic force;

and/or wherein, in certain embodiments, said physical analysis method comprises determining an interaction of two or more hydrophobic and/or partially hydrophobic residues and/or regions of a protein and/or polypeptide that is predicated upon the existence of a bubble and/or an extension of the existent bubble that is dependent on the electric field strength or the distribution pattern of charged residues located between said two hydrophobic and/or partially hydrophobic residues;

and/or wherein, in certain embodiments, a computer code simulates said physical analysis method comprising determination of an interaction of two or more hydrophobic or partially hydrophobic residues and/or regions of a protein and/or polypeptide that is predicated upon the existence of a bubble and/or an extension of an existent bubble that is dependent on the electric field strength or the distribution pattern of charged residues located between in between said two hydrophobic and/or partially hydrophobic residues where said bubble or extension of said bubble is predicated upon the surface tension and/or surface energy of the environment;

and/or wherein, in certain embodiments, said physical analysis method comprises determining diffusion of one region of a protein, and/or polypeptide relative to another region utilizing a speed of motion dependent upon a mobility, the strength of the motive forces present, the viscosity of the solvent and/or changes in global energy terms such as but not limited to the global entropy;

and/or wherein, in certain embodiments, said computational method representing said physical diffusion of one region of a protein, and/or polypeptide relative to another region by a speed of motion dependent upon a mobility, the strength of the motive forces present, the viscosity of the solvent and changes in global energy terms such as but not limited to the global entropy, comprises performing a trial move to determine whether it increases or decreases a global energy term, restoring the system to the state prior to the trial move, and then moving the system again with a mobility that is corrected for the projected change in said global energy term.

The accompanying drawings, which are incorporated and constitute part of this disclosure, illustrate preferred embodiments of the invention and serve to explain the principles of the invention.

DETAILED DESCRIPTION

Figure 1:
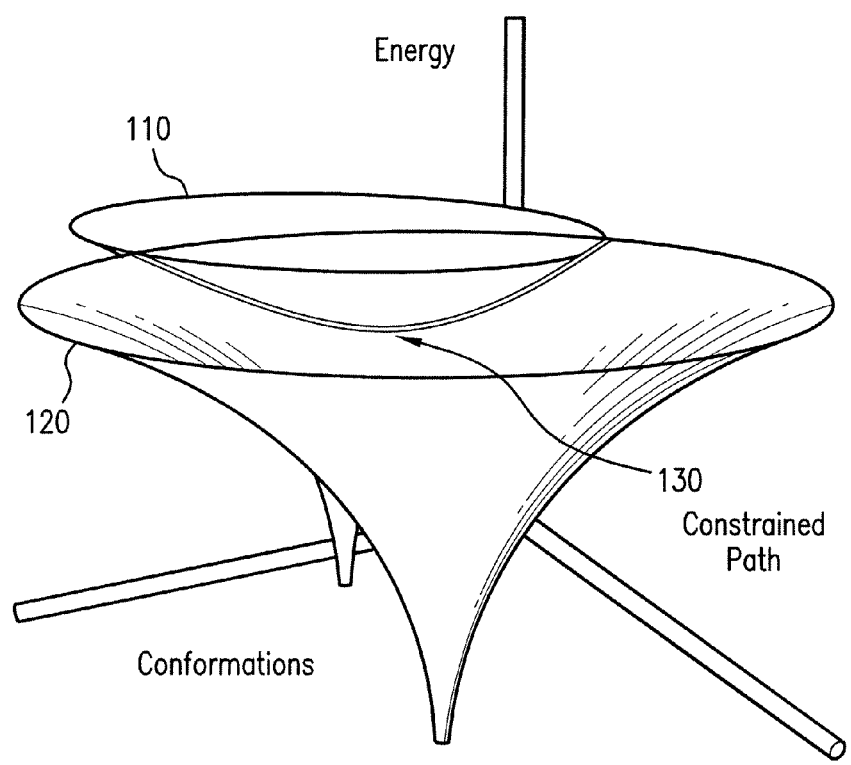
FIG. 1 is an illustrative embodiment of a representation of two internal energy types (shown as cones) of a protein as a function of its conformation (shape). The energy gradient (or force) is found along the curve formed by the intersection of the two energy surfaces.

While the present invention will now be described in detail with reference to the Figs., it is done so in connection with the illustrative embodiments.

The present invention provides for a method to determine the native structure of a polypeptide and/or protein, its structural response to an altered environment, and an altered new equilibrium structure resulting from the altered environment. The method comprises a protein model and a simulation algorithm involving one or more of thermodynamic energy type partitioning, an energy gradient, energy constraints and experimentally observable quantities including but not limited to viscosity, temperature, equilibrium vapor bubble concentrations, molecular diffusion and drift rates.

The invention may be used to predict polypeptide shape change and folding rates resulting from an environmental impetus including but not limited to protein-protein proximity and/or solution characteristics such as pH, temperature, illumination, electric and magnetic fields. For example, when external electric fields approach the (very large) values seen in the close proximity to a point charge (e.g., $1.4 \times 10^{11}$ N/C) the vapor filled alpha helix core of a protein may collapse if the energy stored in the polarized water can exceed energy gains realizable by coalescence of vapor/non-vapor interfaces. Magnetic permeability of the water can produce a similar effect in very strong magnetic fields. Light of an ionizing energy type can create new charged residues and/or species, thereby promoting and/or inhibiting alpha helix and/or beta sheet formation.

The analytic method in this invention is based on a kinetic description of molecular system evolution, which employs an equilibrium reference framework and a mode of motion along the free energy gradients, the speed of which is connected to the mobility of the moving particles. The root-mean-square or RMS volume (the average distance between the atomic constituents of the protein under consideration), is used as a measurement of the amount of protein folding when starting form a known denatured linear state.

Consider the onset of folding in response to an environmental change. The protein begins in a known denatured state. When starting from a linear protein in ambient conditions consistent with a linear structure (for example a protein in liquid water near but below boiling temperature), said linear structure represents the structure with the lowest conformational free energy. The protein is now placed in ambient conditions consistent with a different, necessarily more compact structure than the previous maximum RMS volume linear state. Under the new environment, the old protein shape is no longer than of the lowest conformational free energy and therefore is unstable, and the protein will compact, thereby reducing its conformational free energy. The energy reduction is comprised of, but not limited to, electrostatic free energy, hydrophobic energies (dependent on the environment, not the protein structure), van der Waals forces, and entropy (such as the number of kink sites, vibration spectra, rotational and translational entropies). It is therefore convenient to consider said energy changes to be a function of the RMS volume during protein compacting or folding.

Protein folding and unfolding can be viewed as symmetrical responses of a protein to an environmental impetus. Even when such folding and unfolding is caused by rapid environmental change, it may be treated as a series of small environmental changes and corresponding symmetrical responses of the protein. The protein will take a path along the slope of free energy surface to achieve a new stable shape. If we have two or more distinct energy types, the conformation shape-energy surface for each type can be plotted, and the path constraint one energy-type partition imposes on the other is illustrated in FIG. 1, where the intersection of the two conformation shape-energy surfaces 110 and 120 define the available lowest energy state, and the path would be along the curve 130 that forms at said intersection, as illustrated in FIG. 1. Free energy gradients may be used to define the available lowest energy state, and the minimum and maximum found along the contour. Motion along the intersection curve involves changes (gradients) in both energy types. In this invention, said two distinct energy types can be intramolecular energies and background thermal energies.

The algorithm used in this invention is based on the cooperative motion of a large group of atoms about each of the Ramachandran (dihedral) $\phi$ and $\psi$ angles with a speed that is determined jointly by the mobility of the protein molecule, which mobility is dependent on the characteristics of the solvent, temperature and/or internal energy change with respect to the change in density of charged residues, and by one or more forces derived from internal energy force fields, including but not limited to bonding energies and hydrophobic interactions. Each dihedral angle can have independently a zero or non-zero bonding energy associated with rotation. In the algorithm, the bond rotation energy is typically set to zero. The combined forces acting on atoms, groups of atoms, and/or amino acid residues on opposing sides of the dihedral angle axis produce torques acting upon effective lever arms of the protein, thereby folding the protein to its native shape.

The present invention also provides for an algorithm implemented in a source code that translates said physical description into a series of commands that, upon input of a particular protein and/or polypeptide amino acid sequence; an optional input of temperature; an optional input of diffusion constant and/or an optional input of global energy change upon folding will produce a folded structure of said input amino acid sequence under the input parameters. Global energy change can be inferred from experimental results (as the energy released by the folding of a protein), or it may be treated as a parameter to be revealed by the simulation when examining a protein with a known structure or the known reaction of a protein structure to a known environmental impetus. Additionally, when both the structure and the global energy change are unknown, a number of potential structures predicated on different global energies may be generated. The span of these potential structures is in-turn predicated on the actual relative strength of the global energy to specific electrical, hydrophobic, or other defined energy terms.

Figure 2:
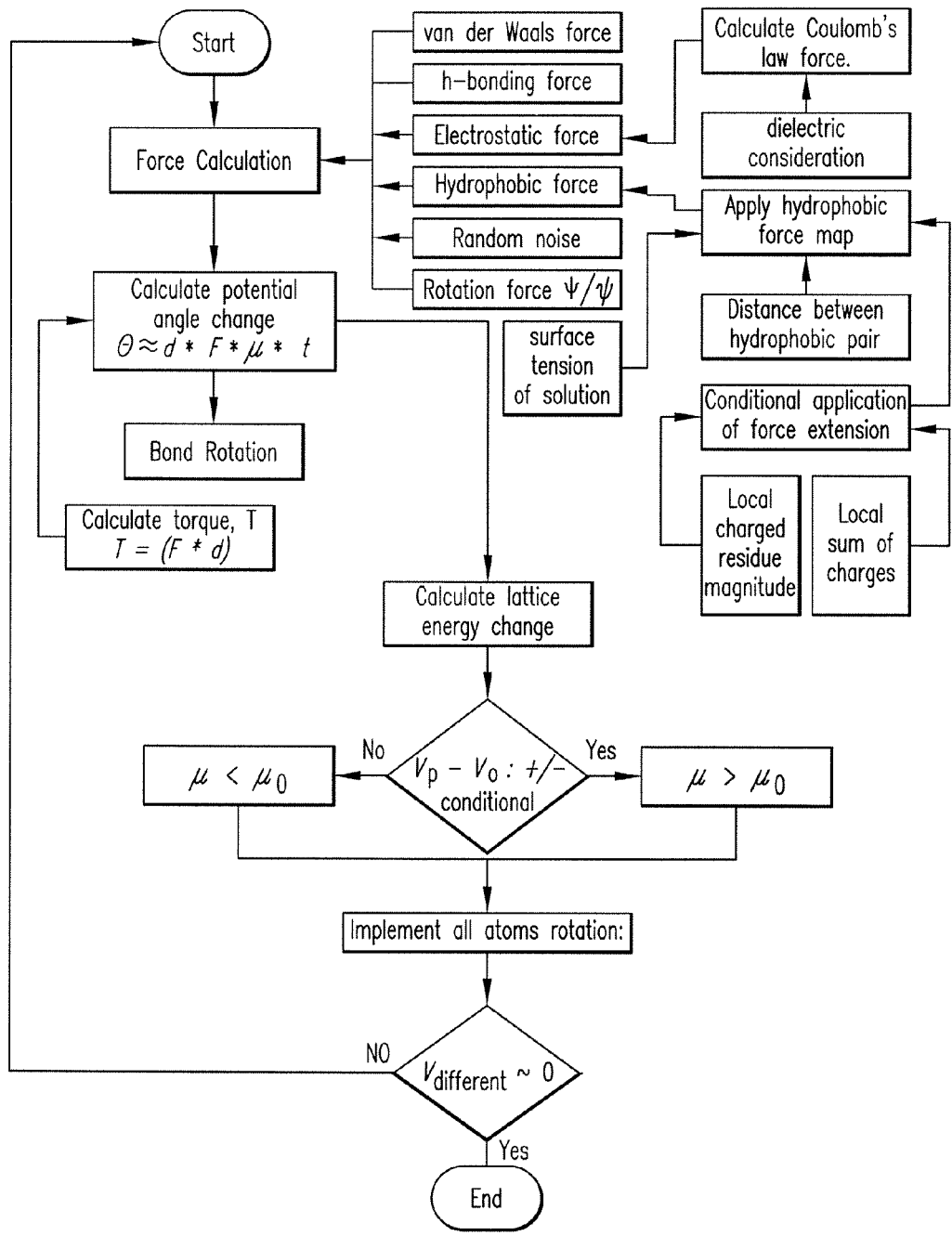
FIG. 2 is a flowchart illustrating an embodiment of an exemplary simulation process employed to model protein folding and secondary structure formation in accordance with an aspect of the present invention.

The algorithm used in this method is based, in part, on physical drift and diffusion via change of the Ramachandran (dihedral) angles on the polypeptide or protein backbone, which corresponds to a cooperative (multi-atom) motion. As illustrated in FIG. 2, the algorithm starts from an arbitrary conformation and eventually transforms a protein molecule into its final folded state through successive steps which are linked to real time. In each step, the algorithm computes internal forces resulting from the particular conformation taken by the protein molecule as well as an effective random force resulting from the random collision of the protein with the surrounding media, typically water. The algorithm then moves the molecular segments on either side of the alpha carbon bond pair having the largest net torque (sum of the actual force and the random effective thermal force multiplied by the appropriate lever arm length) relative to one another for the duration of a time step along a chosen dihedral angle by $\theta$ ($\theta=d/l$, where d is the displacement of a moving particle in thermal diffusion, and l is the effective lever length of the protein).

Figure 3:
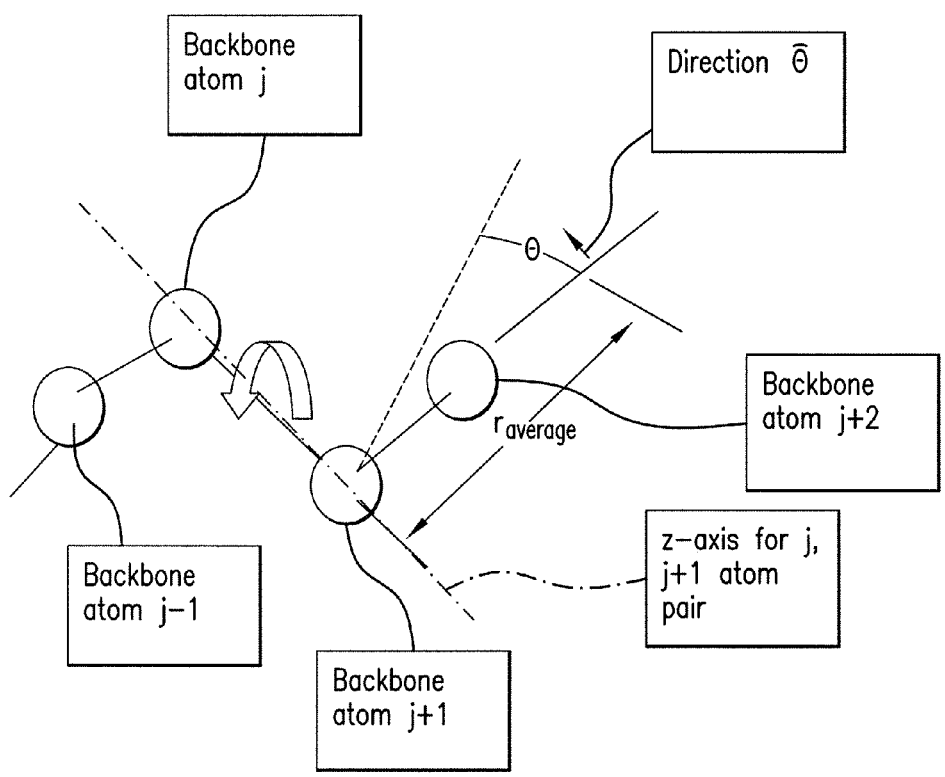
FIG. 3 is an illustrative diagram of the calculation of torque about a backbone carbon pair created by forces acting on a protein.

A diagram of the calculation of torques on each backbone atomic pair is presented in FIG. 3. A cylindrical coordinated system is defined for each atomic pair, for example atomic pair j, and j+1 of FIG. 3. Where the z-axis of said cylindrical coordinate system is defined in the direction of the bond between said atomic pair j and j+1.

In terms of said coordinate system the torque generated about said axis defined for said atomic pair j and j+1 is a product of the torques and/or forces generated between every atomic pair i, j+n where i ranges from 1 to j−1 and n ranges from 2 to the number N where M=N+j and M is the number of backbone atoms in the protein and/or polypeptide. That is, forces existent on atoms and residues on one side of the atomic pair j and j+1 interact with those on the other side. Forces directly on atom (and residue if any) j and atom (and residue if any) j+1 do not generate a rotational torque about said atomic pair axis and are therefore not counted in the force or torque generation.

Said forces and/or torque is predicated upon the charges attached to said pairs i, j+n found on either side of atomic pair j and j+1 and/or the charges attached to residues attached to said pairs i, j+n and/or the degree of hydrophobicity of said residues attached to every said pairs i, j+n, other forces such as but not limited to hydrogen bond related forces may also be considered.

Torque generated about axis z for said atomic pair j and j+1 is a product of the force generated by every said pair i, j+n for every allowed i and n value. Only the force components, $F_{\theta i,j+n}$, in the direction $\hat{\theta}$ produces torque about said axis z for said atomic pair j and j+1. Said forces may be dependent on said distance between said pairs i, j+n. The total torque about said axis may be defined for said atomic pair j and j+1 as:

$$T_{j,j+1} = \sum_{i,j+n} F_{\theta i,j+n} \times \left(\frac{r_i + r_{j+n}}{2}\right)$$

$$F_{avej,j+1} = \frac{T_{j,j+n}}{r_{ave}}$$

It is possible to accurately determine $r_{ave}$ by summing the values of $r_i$ and then dividing by the number j−1 to determine a value of $n_{i\ ave}$ and then summing the values of $r_{j+n}$ and then dividing by M−J−1 to establish a value for $r_{j+n\ ave}$ followed by the averaging of two said average values. The various average length, $r_{ave}$ may be set as half of the length of the denatured protein or the approximate radius of a partially compacted protein in order to speed calculation. Other fixed or variable $r_{ave}$ values such a number that is average for proteins of a given type or size are also may also be used. Other reasonable schemes for calculation of the torque and the radius arm through which it is applied can be used.

The simulation moves by rotation about one axis z for one said atomic pair j and j+1 per time step. The particular axis z for said particular atomic pair j and j+1 selected for rotation on a given time step is determined by tabulating the values of $T_{i,i+n}$ for every backbone pair and then adding a random torque value consistent with thermal energy, kT, the product of the Boltzmann constant and the Kelvin temperature used for the simulation.

In one time step there are M−1 axis associated with M−1 torque calculations to each a random thermal energy is added yielding an adjusted torque values, $T_{i,i+n}$, that are then tabulated. The atom pair having the largest adjusted torque value is allowed to move for a time period, t, according to said angular displacement formula:

$$\theta \approx \sin\theta \approx \frac{\mu F_{avei,i+n}t}{r_{ave}}$$

Where µ is the mobility applying to force type $F_{ave\ j,j+1}$ which may be a function of a second energy consideration and other terms such as but not limited to the viscosity of the environment as discussed below.

Figure 4:
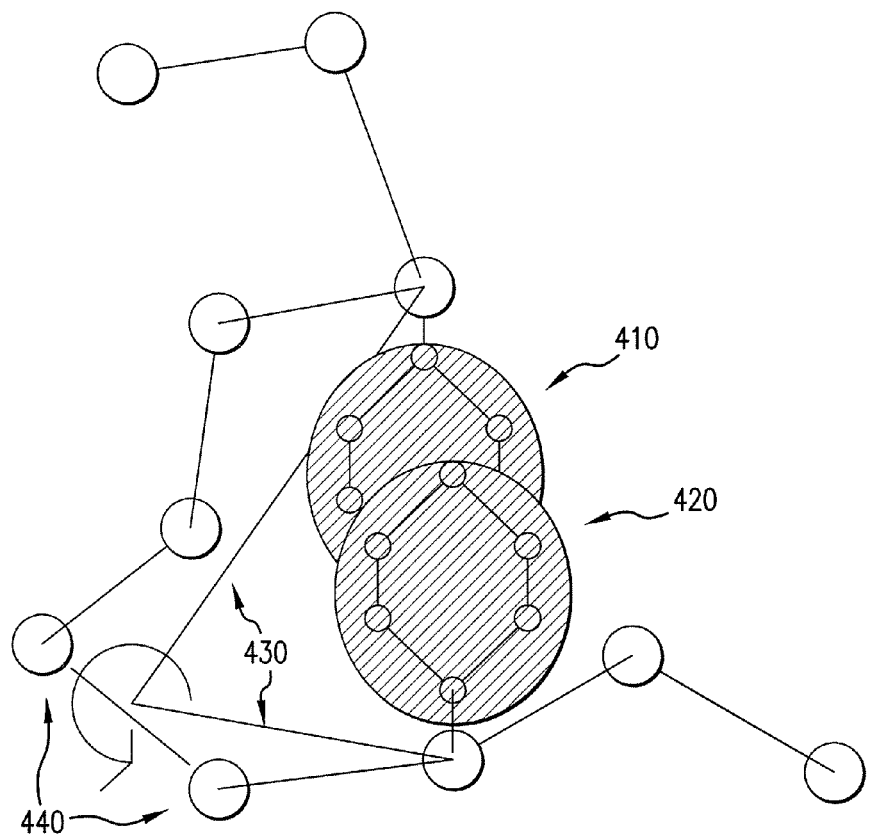
FIG. 4 is an illustrative diagram of a protein conformation change through rotation around a Ramachandran angle about an alpha carbon backbone bond pair induced by the resolved torque operating on the bond that may be implemented in the flowchart of FIG. 2.

This mode of move on a protein molecule is illustrated in FIG. 4 (wherein amino acid side chains are represented as aromatic rings). These hydrophobic residues (410 and 420) come into direct contact, whereupon the two bubbles or internal surfaces of the water/hydrophobic interface coalesce, thereby exerting a force (as indicated by lines 430) on a distant alpha carbon pair under consideration (440). The torque about the bond axis of alpha carbon pair 440 generated by the coalescence of hydrophobic residues 410 and 420, as well as any reduction of that torque caused by the coalescence, and all other possible alpha carbon bonds that may be influenced by the coalescence is calculated as in FIG. 3. The global energy also involves density dependent entropy. In cases where this entropy cannot be determined from experimental results, a trial move is applied, the approximate density calculated using an average mobility, and the change in entropy determined, then the actual rotation is performed using an appropriately modified mobility. The process is repeated until a fixed number of time steps have been performed or the structure ceases to change conformation with respect to predetermined volume criteria (for example, a fraction of the RMS volume) for a fixed number of time steps.

In the above procedure, the displacement d of a moving particle in thermal diffusion is a function of the diffusion constant and time t, $d \approx \sqrt{Dt}$, where D is the diffusion constant and t is the time step used in the simulation, e.g., $10^{-7}$ s, which when sufficiently short invokes the preceding approximations. A reasonable range for t is from $10^{-13}$ s to $10^{-3}$ s. The diffusion constant used may be the known diffusion constant of a similarly sized protein. Alternatively, the diffusion coefficient could be treated as a simulation fitting parameter that can be used to adjust the amount of folding that occurs in a particular time step. Also alternatively, the diffusion coefficient could be calculated from first principals such as the Einstein approach (e.g., $$D_{rms} = \sqrt{\frac{kT}{3\pi\eta a}}\sqrt{t}$$

where η is the viscosity of the liquid, a the radius of the protein, k is Boltzmann constant, T the temperature in Kelvin, and t is time. See Taylor, Zafiratos, Dubson, Modern Physics for Scientists and Engineers $2^{nd}$ ed. Prentice Hall Inc NY 2004, p. 105).

The effective random force such that the same displacement would be produced as if the protein backbone atoms were undergoing random thermal diffusion is then determined as a Gaussian distribution about an average effective force $$F_{eff} \approx \pm kT\sqrt{\frac{1}{Dt}}$$

(because d=μF$_{eff}$t), where k is Boltzmann's constant and T is the temperature in Kelvin degrees. Correspondingly, the average torque (the product of force and distance) that acts upon about each Ramachandran axis is $$F_{eff} \times r = \pm r_0 kT\sqrt{\frac{1}{Dt}}$$

where r$_0$ is the average length of the lever arm through which the force acts. In the case of Ubiquitin a value of $10^{-6}$ cm is reasonable. When D is $10^{-5}$ cm$^2$/s, t, one computational time step, is $10^{-7}$ s, and T is 300° k a torque value of $$\frac{kT}{cm} cm,$$

is obtained.

Figure 5:
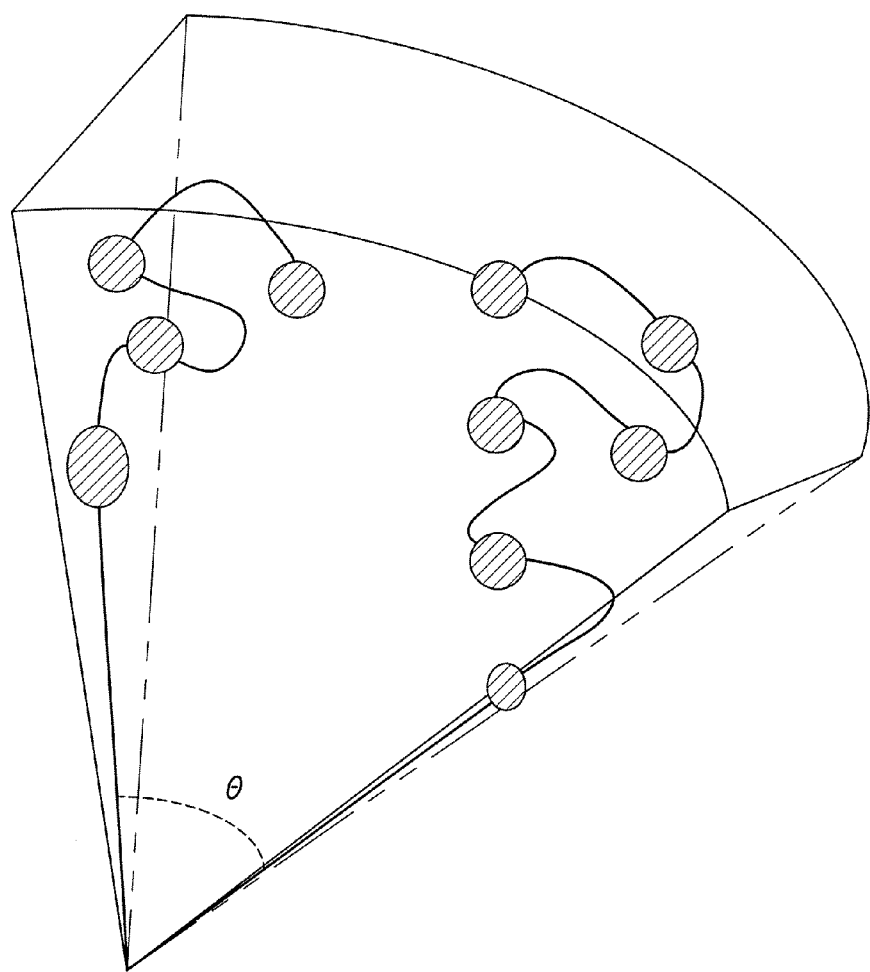
FIG. 5 is an illustrative diagram of the effect of thermal induced Ramachandran angle change on protein density useful for calculating the force equivalent of thermal energy.

Another approach yielding a similar result is based upon the force necessary to exactly counteract diffusion. Since drift and diffusion must be balanced at equilibrium, D∇n=μF$_{eff}$, where n for this consideration is defined as $$n = \frac{N}{V_m}$$

and where N is the number of atoms in the protein and V$_m$ is the volume of the molecule with respect to the Ramachandran angle as seen in FIG. 5, $$V_m = \int_0^r \int_0^\theta \int_0^\delta r\, dz\, d\theta\, dr = \frac{r^2}{2}\theta\delta.$$

Here θ is the Ramachandran angle under consideration, r is the average length of the protein as measured from the axis of rotation and δ is the average thickness of the wedge shaped volume, as illustrated in FIG. 5. Therefore, volume is predicated on angle change since $$n = \frac{N}{\left(\frac{r^2}{2}\theta\delta\right)}$$

$$\therefore$$

$$\nabla n \approx \frac{1}{r}\frac{d}{d\theta}\left(\frac{N}{\frac{r^2}{2}\theta\delta}\right) = \frac{-N}{\left(\frac{r^3}{2}\theta^2\delta\right)}$$

Substitution of this equation into the balance of drift and diffusion also using the Einstein relation yields:

$$D\frac{-N}{\left(\frac{r^3}{2}\theta^2\delta\right)} = \mu\left(\frac{N}{\frac{r^2}{2}\theta\delta}\right)F_{eff}$$

$$\therefore$$

$$F_{eff} = \frac{-D}{\mu\theta} = -\frac{kT}{r\theta}$$

Thus the torque acting on the axis of the Ramachandran angle corresponding to this effective force is F$_{eff}$r=kT/θ, where θ runs from 0 to π with a central value of π/2 being a reasonable estimate producing a torque value approximately equal to kT.

Energy-Coupled Mobility Determination

Einstein relations express the strict relationships between field driven drift mobility and diffusion constant for probabilistic particle motion (See Albert Einstein, Annalen der Physik, 17, 549 (1905); Richard J. Borg and G. J. Dienes, "*An Introduction to Solid State Diffusion*" Academic Press, NY 181 (1988) ("Borg & Dienes"); Paul G. Shewmon, *Diffusion in Solids*, McGraw-Hill, NY 24 & 140 (1963) ("Shewmon"). For example, the energy conservation consideration can be applied to the steady-state distribution of mobile electrons under the attraction of an opposite charge at a fixed position. The steady-state diffusion current (electrons diffusing away from the attractor) balances the drift current (electrons moving towards the attractor), leading to a net zero energy transport. Here an external electric field is present. In another example, the charges carried by an atomic site on a protein molecule may move via energy absorbing (or releasing) reconfiguration. A charged protein region moving relative to the rest of the protein produces a changed structure characterized by changed distributions of kinks, twists and/or rotated bonding sites.

Consider the simple case of a system having a mobile charged species, with no matrix coupling, and moving under the influence of an electric field (the gradient of an electric potential). Using Onsager relation (e.g., see Borg & Dienes and Shewmon), the drift current $\vec{J}_{drift}$ of an ensemble of charged particles having a density n$_p$ and in an electric field $\vec{E}$, is:

$$\vec{J}_{drift} = -n_p\mu\vec{E} \quad (1)$$

where μ is the mobility of the charged species with respect to the electric field. Fick's relation for the random-walk-like diffusion current, $\vec{J}_{diff}$ of this charged species is proportional to the product of the gradient in species density (or concentration), ∇n$_p$ and a diffusion constant D:

$$\vec{J}_{diff} = -D\nabla n_p \quad (2)$$

The total current, $\vec{J}_{Total}$ at a particular location is $$\vec{J}_{total} = -n_p\mu\vec{E} - D\nabla n_p. \quad (3)$$

In steady state, the total flux must be zero:

$$\vec{J}_{total} = 0 = -n_p \mu \vec{E} - D\nabla n_p. \quad (4)$$

Therefore:

$$n_p \mu \vec{E} = -D\nabla n_p \quad (5)$$

or $$\mu \vec{E} = -D\nabla(\ln(n_p)). \quad (6)$$

Next, the electric field is defined as the gradient of the electrostatic potential energy:

$$\vec{E} = \nabla \phi_{pot}. \quad (7)$$

Combining equations 6 and 7 yields:

$$\vec{E} = \nabla \phi_{pot.} = -\frac{D}{\mu} \nabla (\ln(n_p)). \quad (8)$$

Defining an electrostatic chemical potential in terms of the density of charged particles, n, and the electrostatic potential, $\phi_{pot}$:

$$\phi_{echem.} = \phi_{pot.} + kT(\ln(n_p)). \quad (9)$$

The first term on the right hand side of equation 9 is the internal energy term (e.g., the Fermi level for electrons and holes) and the second term is the entropy of mixing term. Equilibrium requires that both the net current fluxes and the chemical potential gradients of the relevant charged species be zero whenever there is no compensating gradient in the matrix chemical potential:

$$\nabla \phi_{echem.} = \nabla \phi_{pot.} + kT\nabla(\ln(n_p)) \quad (10)$$

$$= -\frac{D}{\mu}\nabla(\ln(n_p)) + kT\nabla(\ln(n_p))$$

Equation 10 is solved in the case of a zero matrix free energy change $\nabla \phi_{echem} = 0$:

$$\frac{D}{\mu} = kT \quad (11)$$

This is the well-known Einstein relation. When there is an energy coupling between charged species and the matrix in which in moves, the matrix free energy consideration must be formulated. Following the definition of thermodynamic terms used by Dickerson, the free energy, G, and the change in free energy, dG, induced by a change in the environment (i.e., external electric fields, temperature, pressure, etc.) can be expressed in terms of chemical potentials as:

$$G = -ST + VP + \sum_i \phi_{echem_i} n_i + \sum_j \phi_{L_j} n_j + \sum_k \phi_{O_k} n_k \quad (12)$$

and $$dG = -SdT + VdP + d\left\{\sum_i \phi_{echem_i} n_i\right\} + \sum_j \phi_{L_j} dn_j \quad (13)$$

where in equation 13 the contribution by charged particles to the change in free energy is expressed in the summation of $\Sigma \phi_{echem}$, and the chemical potentials related to non-electrostatic effects such as strain fields in the material matrix are expressed in the second summation, $\Sigma \phi_L$, whereas all other chemical potentials related to the matrix (but not a function of charge particle density in any way) are represented in the final summation. (See Richard E. Dickerson, *Molecular Thermodynamics*, W. A. Benjamin, Inc., Menlo Park, Calif. 249 (1969) ("Dickerson").

While the atmospheric pressure dependence of VdP is not expected to be a large factor in solid matrix systems, the induced strain fields may be. Therefore, the present formulation retains the term VdP. Note that the full differential of the electrostatic chemical potential must be maintained because changes in the local and global electric field affect the free energy contribution of these charged species and the electric field will be an implicit consideration of the ensuing formulations.

With an eye towards spatial dependent perturbation applications (such as a system in an applied external field) the free energy gradient generated between a reference state (and/or location within the material matrix) and a perturbed state (and/or location within the material matrix) is determined:

$$\nabla G = \nabla \left\{ VP - ST + \left( \sum_i \phi_{echem_i} n_i + \sum_j \phi_{L_j} n_j \right) \right\} \quad (14)$$

Equation 14 provides a mathematical basis for a system in equilibrium and is assumed to be applicable to a system perturbed slightly from equilibrium. In equilibrium the free energy has the same minimum value at any arbitrary position in the system, so $$\nabla G = \nabla \left\{ VP - ST + \left( \sum_i \phi_{echem_i} n_i + \sum_j \phi_{L_j} n_j \right) \right\}_{\forall x_i, y_i, z_i} = 0 \quad (15)$$

Since every point in a protein (or polypeptide) is in thermal contact with every other point, and since the protein is free to change shape (to a degree free to move), when motion ceases or begins to fluctuate about a given shape, it is necessarily the case that forces have ceased. That is, the forces (generally free energy gradients) arising from a steady-state and/or equilibrium state sum to zero. Therefore a small localized (non-uniform) change in the environment (e.g., a localized temperature change) that induces a change in the energy stored in the matrix strain fields about charges results in motion of charged particles. These motions cease when an equilibrium condition is established that has a net zero free energy gradient as well as having a net zero current. Interestingly, the protein's shape may oscillate about a given shape, but the energy of this oscillation must in turn be consistent with the temperatures (~kT). Such oscillation is physical and possible in real protein systems and is possible in the simulation.

The speed of a return to steady-state (equilibrium here) when a perturbation is introduced can be used to define mobility. The speed of s charged particle moving in a free energy gradient (and/or an electric field) is dependent on both the free particle speed and the speed at which the matrix can respond to charged particle redistribution. When in true equilibrium, this responding speed can be obtained by assuming it is equal to the speed of motion of the charged particles. Using equation 10 and equation 15 yields:

$$\nabla G = \left\{-\frac{D}{\mu} + kT\right\}\nabla \ln n_p + \nabla\left\{VP - ST + \left(\sum_j \phi_{L_j} n_j\right)\right\}_{\forall x_i, y_i, z_i} = 0 \quad (16)$$

Equation 16 expresses the fundamental relationships between kinetic factors that equilibrate fluxes of charge particles and thermodynamic factors that couple the matrix to the particles. Rearranging equation 16 and solving for the mobility yields:

$$\mu = \frac{D\nabla \ln(n_p)}{\nabla\left\{VP - ST + \sum_j \phi_{L_j} n_j\right\}\Big|_{x_1, x_2, x_3 \ldots x_n} + kT\nabla \ln n_p} \quad (17)$$

When there are no strain or other couplings to the matrix (i.e., when the value of the terms bracketed in the denominator), equation 17 reverts to the well-known Einstein relation, $\mu = D/kT$.

Use of this energy-coupled mobility by a simulation of Ubiquitin, a single chain polypeptide composed of 74 amino acids, is demonstrated here as a non-limiting example. The simulation is conducted according to the algorithm described above, and the mobility is determined according to equation 17 to account for global changes induced by shape change. In a hypothetical situation in which only entropy changes with volume, where $\nabla H=0$, and where $\nabla S$ can be expressed as $n_k$ (here the product of the number of kink sites and the entropy value for a site):

$$\nabla S = \nabla n_k \approx \frac{1}{r}\frac{\partial n_k}{\partial r} \quad (18)$$

Simplification of equation 17 yields $$\nabla \ln n_p \approx \frac{1}{r}\frac{\partial \ln n_p}{\partial r} \approx \frac{1}{r}\frac{\partial \ln n_p}{\partial n_k}\frac{\partial n_k}{\partial r} \quad (19)$$

Therefore equation 17 becomes:

$$\mu \approx \frac{D}{kT\left(1 - \frac{\partial n_k}{k\partial \ln n_p}\right)} \quad (20)$$

Thus obtained mobility $\mu$ is incorporated into the algorithm described above.

Figure 6A:
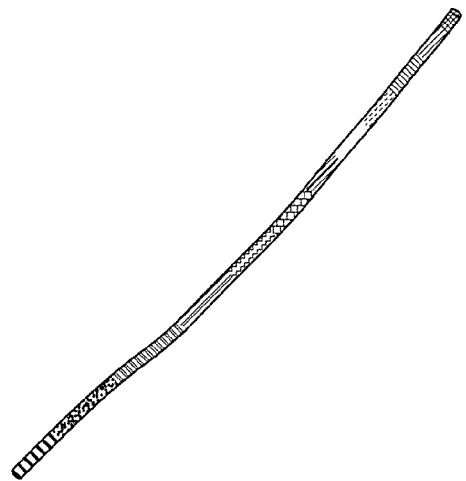
FIG. 6 is a representation of the simulated results of Ubiquitin folding produced by one embodiment of the invention: the linear Ubiquitin as the starting structure in (A); a constant mobility, i.e., $\mu = D/kT$, is used for all conformational changes of the protein, in (B); a greater mobility (2.5 fold relative to the $\mu$ value in case B) is used for contraction while a smaller mobility (0.71 fold relative to the $\mu$ value in case B) is used for expansion, in (C).
Figure 6B:
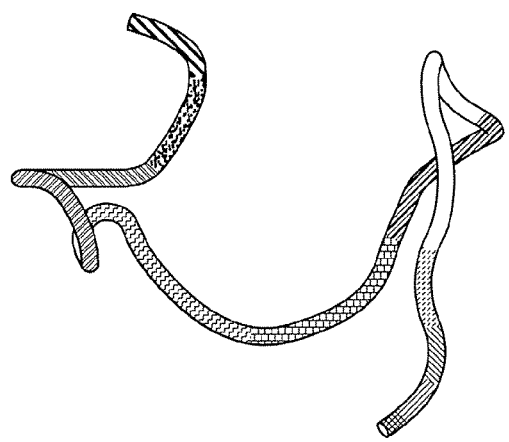
Figure 6C:
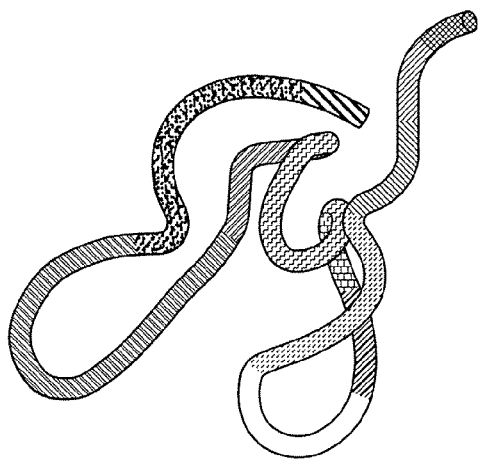

FIG. 6 shows a linear illustration of Ubiquitin in (A); the result of a folding simulation using a constant mobility $\mu=D/kT$ in (B), where diffusion constant D is obtained from Dwight E. Gray, Coordinating Ed., *American Institute of Physics Handbook* 3rd., McGraw Hill, NY, 2-206 (1972); and the result of a folding simulation using a variable mobility $\mu$ (in equation 20) where $$\frac{\partial n_k}{k\partial \ln n_p}$$

is assigned the values of −0.6 under contraction and +0.6 under expansion (in order to illustrate the impact of this parameter on structure generation), in (C). The corresponding faster contraction relative to expansion results in a more compact structure with a volume of 0.33±0.16 (arbitrary units averaged over 20 simulations) compared to 0.54±0.23 for the constant mobility case. The speed of motion is important because it impacts the distance moved in a given time step, the motion always choosing the largest force according to the simulation design. The largest speed produces the largest displacements, which in-turn produce the greatest energy reduction. Therefore higher speed in one direction relative to another will produce a structure automatically having a lower energy.

The energy term in the mobility equation (here the entropy term) is also considered. The entropy term attempts to express an energy reduction (which the formulation accounts for in speed) as a result of a more compacted structure (where there is greater entropy and therefore lower free energy) when steady-state is reached. It is possible to determine the free energy of folding (minus the electrostatic energy change) entirely or in part by experiment, such as from measurement of the heat of folding minus an inferred electrostatic energy change predicated on the net electrostatic energy difference between folded and denatured states. The free energy of folding may also be dropped from the energy term if the energy term is dominated by an entropy term that increases upon compaction. It is possible to use the simulation to deduce an effective free energy change (minus the electrostatic energy) by trial and error simulation of protein folding, by matching folded structures and/or folding rates for a protein for which sufficient experimental data is available. Note that neither structure shown here correlates well to the known structure because this example was focused solely on the use of global energy terms. More sophisticated simulations incorporating more force considerations including hydrophobic interactions between protein residues are necessary to produce more accurate molecular shape.

Hydrophobic Interactions Considerations

The well-understood hydrophobic interaction results from water surface produced at interfaces with non-polar and/or un-charged media. Owing to the highly polar nature of the water molecule, such surfaces extract significant energy cost. Each hydrophobic residue on the protein molecule has an effective bubble around it.

Consideration of equilibrium phenomena, such as the vacancy density in solid-state diffusion (see e.g., Shewmon) is typical of the kinetic description. Here the necessary equilibrium consideration involves the density of background bubbles, because the bubbles provide a mechanism for force conveyance. When two bubbles come in intimate contact a force is generated by the surface tension which tends to reduce the surface area of the two bubbles through coalescence.

Figure 7:
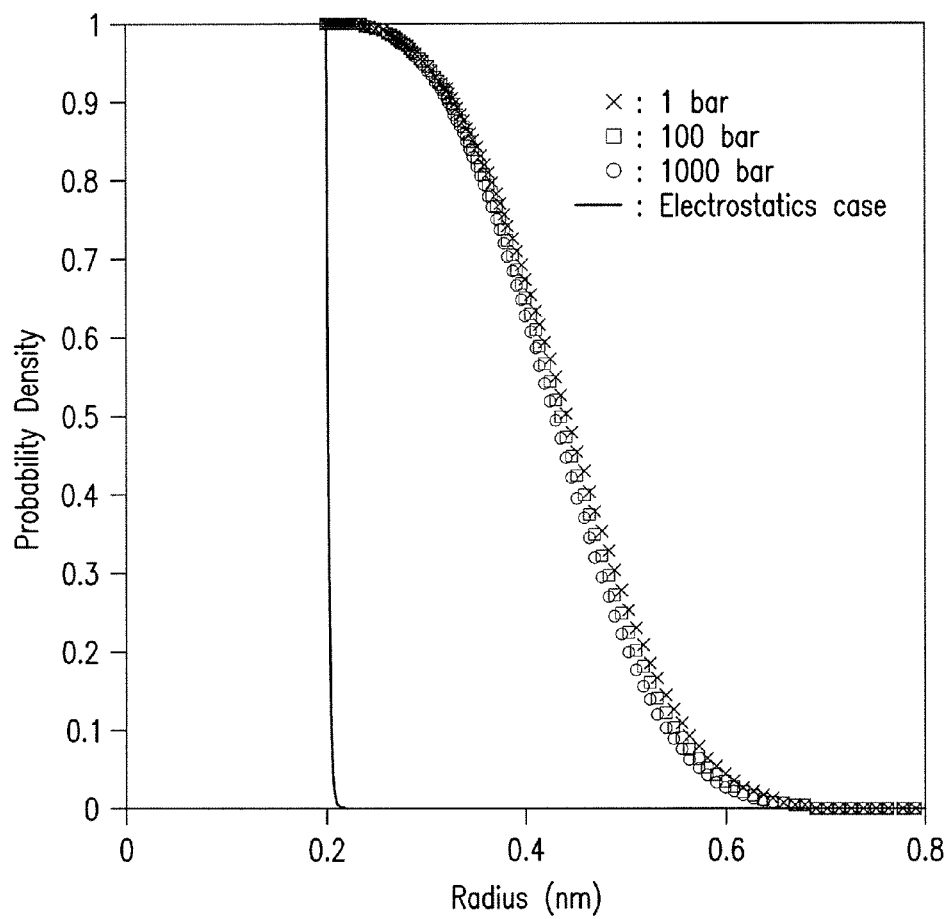
FIG. 7 is an illustrative diagram of the equilibrium probability of finding a water vapor bubble per unit volume and/or per number of water molecules as a function of bubble radius (2*distance) under different pressures in the absence or in the presence of electric fields according to one embodiment of the invention.

FIG. 7 shows the probability of the natural occurrence of vapor bubbles in water as a function of bubble radius (2*distance). The probability is an equilibrium volume probability and it is assumed that there is a bubble of a given radius in a particular water volume when the probability is large (e.g., >0.5), in a manner similar to the vacancies that are present in metals. See Richard J. Borg and G. J. Dienes, *An Introduction to Solid State Diffusion*, Academic Press, NY. When contacting the effective bubbles that encase each of the two hydrophobic residues (FIG. 8) the natural bubble provides a conduit to convey force. Paralleling the formulation of the vacancy in solids described by Hull (David Hull, *Introduction to Dislocations 2nd Ed.* Pergamon Press, NY, 16 (1975)), the equilibrium probability of bubbles (shown in FIG. 7) of a given radius $V_B$ in water can be calculated:

$$\frac{V_B}{V_X} = K = e^{-\Delta G/kT} \qquad (21)$$

where $\Delta G$ is the free energy change for equilibrium between bubbles of size $V_B$ and $V_x$, which can be expressed as $$\Delta G = \int_0^{r_0} PdV + \int_0^{r_0} \frac{2\gamma}{R} dS \qquad (22)$$

where PdV is the work needed to expand a bubble filled with an equilibrium water pressure, $V_x$ is the equilibrium probability of the same volume being filled with water, $\gamma$ is the surface tension of water (~72 dynes/cm), $r_o$ is the radius of the bubble under consideration, and dS is an elemental surface. See Dwight E. Gray, Coordinating Ed., *American Institute of Physics Handbook 3rd.*, McGraw Hill, NY, 2-206 (1972). For a spherical bubble, the elemental surface can be written as:

$$dS = \frac{8}{3}\pi RdR.$$

Bubble densities can also be experimentally measured and/or inferred as a function of bubble radius from direct measurement and analysis of the water or solution under consideration. Also, it is possible to consider bubbles of different shapes and/or the expansion of a given bubble to generate an appropriate force versus distance map for the interaction of two hydrophobic residues. The simulation may also be used to construct an effective force versus distance force map for the interaction of two hydrophobic residues by trial and error simulation of protein folding, through matching folded structures and/or folding rates for a protein for which sufficient experimental data is available.

Bubble formation is affected significantly by electric fields produced by charges, since the electric field tends to draw in the strongly polar dielectric water thereby lowering the energy stored in the electric field. The corresponding energy necessary to remove the water molecules polarized by the electric field must be paid during bubble formation, and is dependent upon the shape of the charged residue or specie, the distance about the charges the water needs to be removed from, the magnitude of the charge, and the distance at which the charged residue or species can be approached by water.

The strength of the electric field created by the charge is dependent upon the distance to the location under consideration, r, and the relative polarizability of the media $\chi$ (usually water, where $\chi=74$):

$$\vec{E} = \frac{k_c q}{\chi r}\hat{r},$$

where q is the charge under consideration in Coulombs (C), r is the distance between the charge and the location under consideration, and r(caret) is the direction in a convenient coordinate system between said charge and said location expressed as a unit vector, and $k_c$ is the Coulomb constant. $\chi$ will vary depending upon the distance, r, as the presence of any water between the charge and the location under consideration is not certain. At 0.1 nm, it is not physically possible for there to be any water in between the charge and the location, so $\chi=1$. At distances of less than ~1 nm, it is possible to calculate the electrical energy reducing polarization by calculating the probabilistic presence of a water molecule and the degree to which it is polarized, so $\chi$ is between 1 and 74. At large distances, $\chi$ can be assumed to be 74.

Accordingly, equation 21 must be modified to reflect the extra energy needed to remove the dielectric (water) from the electrostatic field:

$$\frac{V_B}{V_X} = Ke^{-W/kT} \qquad (23)$$

where W is the work required to transfer a bubble of size $V_x$ from the electric field in water to an electric field in vapor (essentially vacuum). (John D. Jackson, *Classical Electrodynamics*, 3rd edition, Wiley & Sons, NY, 167 (1999)).

Figure 8:
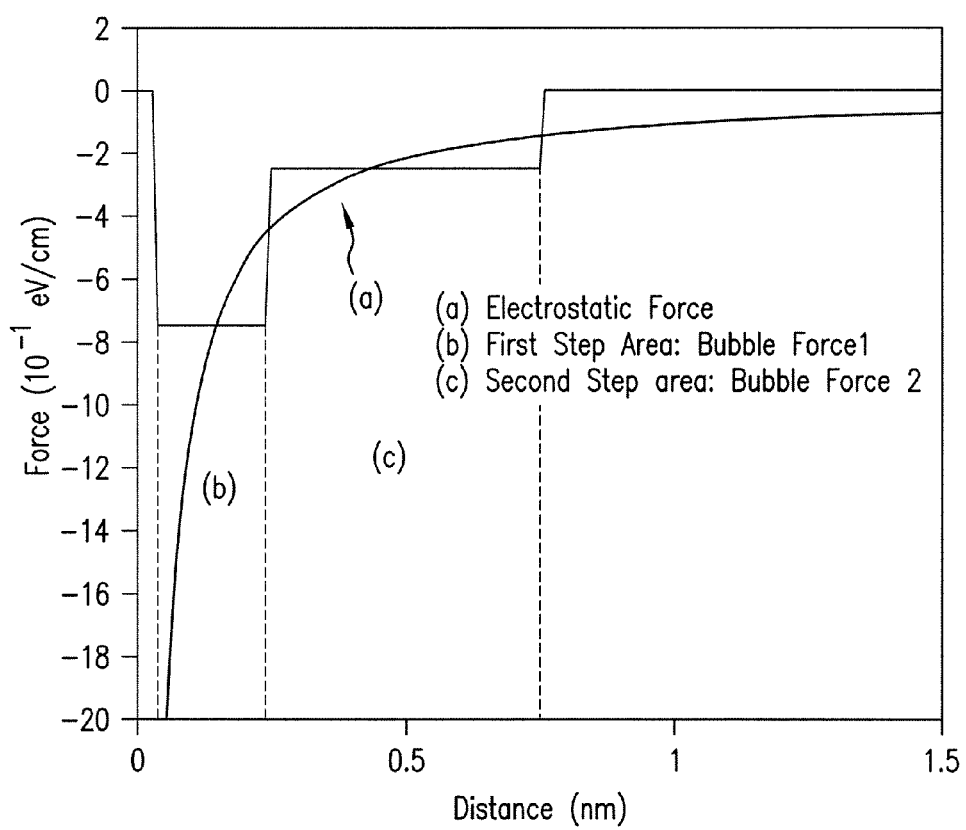
FIG. 8 is an illustrative diagram of the force-distance relationship that may be employed in one arrangement of the method: electrostatic force vs. distance in (A); direct contact hydrophobic force vs. distance in (B); and the conveyance of the hydrophobic force via equilibrium vapor bubble in (C).

Under the condition where a charged residue is characterized by a single electronic charge having a minimum radius of 2 angstroms (diameters smaller than the size of a water molecule are meaningless) and a maximum radius of 1.0 nm (the distance at which bubbles without electrostatic fields begin to show markedly decreased probability as seen in FIG. 7), W is approximately 2.5 eV. Correspondingly the product $Ke^{-W/kT}$ is essentially zero as shown in FIG. 8. Under such condition, bubbles become improbable and hydrophobic force cannot be conveyed in regions having electric fields in the line-of-sight between two hydrophobic residues.

Figure 9:
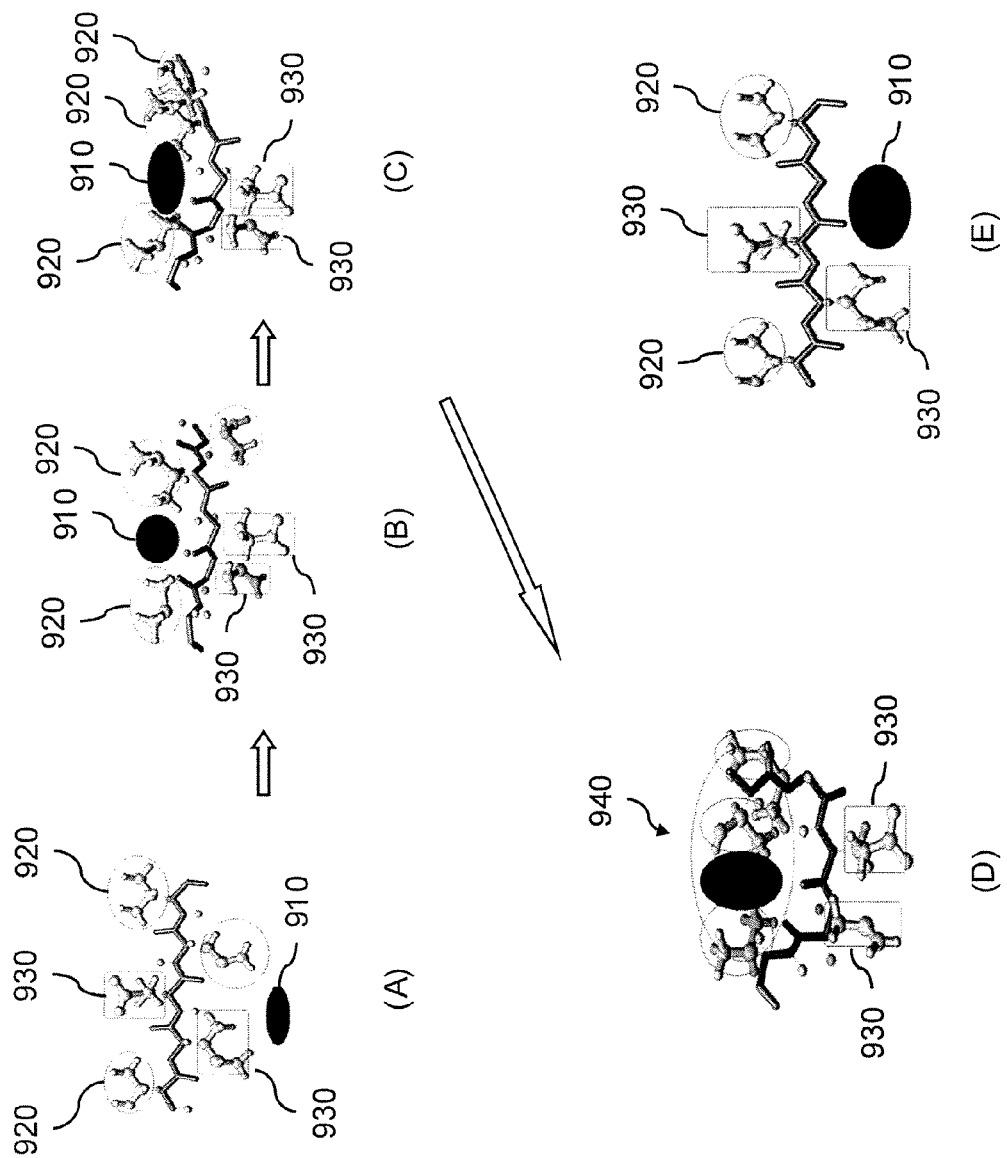
FIG. 9 is an illustrative diagram of simulation steps that may be implemented in one arrangement of the method wherein a vapor bubble (910) is spontaneously generated in the vicinity of two hydrophobic residues (920) in a region known to form an alpha helix (A). The charged residue (930) can move away from the line-of-sight (a line charting the shortest distance between a reference point (e.g., the RMS center) of one hydrophobic residue to another hydrophobic residue) between the two hydrophobic residues by rotation allowing the vapor bubble to insert in the gap (B). The backbone moves in response to the forces generated by the coalescence (940) of the bubbles (C) forming an alpha helix loop segment (D). In (E) a beta sheet region vapor bubble insertion is blocked by one of the two similarly charged residues. Mutual repulsion prevents the movement of both charged residues to a region out of the line-of-sight between the two hydrophobic residues.
Figure 10F:
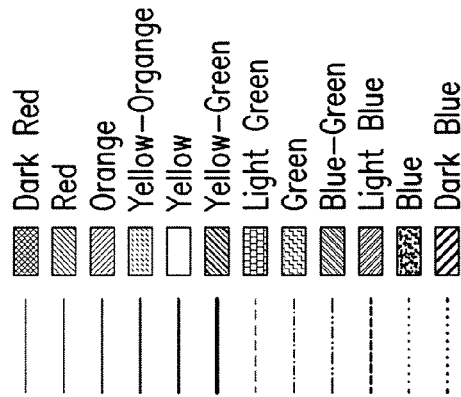
FIG. 10 is an illustrative diagram of the folding of Ubiquitin under different modeling conditions that may be implemented in one arrangement of the present invention: electrostatic interaction only in (A), hydrophobic forces represented by a single square well, plus electrostatic interactions in (B), bubble extended two square well hydrophobic forces in (C), bubble extended two square well hydrophobic forces with intervening charge conditional extension rule and electrostatic forces in (D) (1040 and 1060). A Pymol illustration of the experimentally determined Ubiquitin structure is provided for comparison in (E) and (F) (1050 and 1070).
Figure 10F:
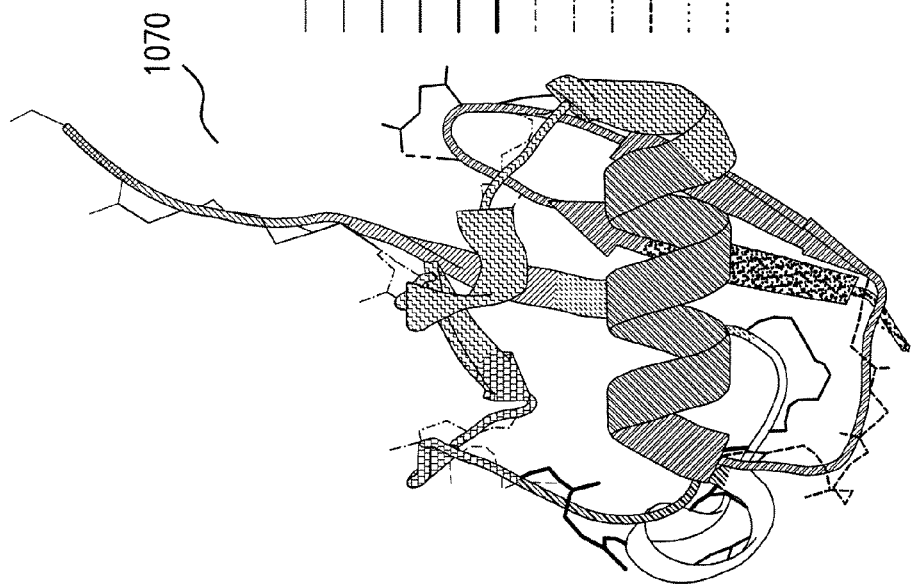
Figure 10F:
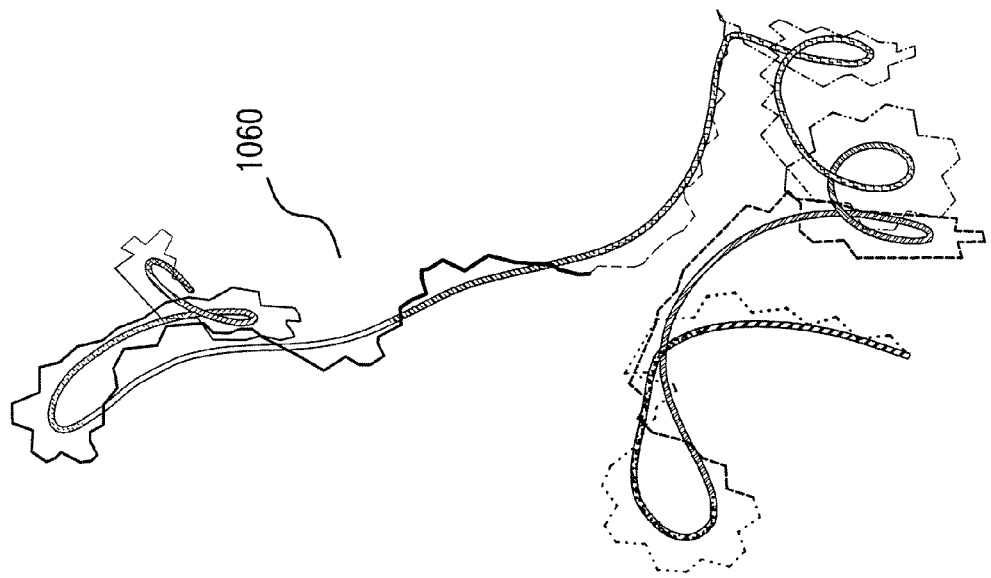
Figure 11:
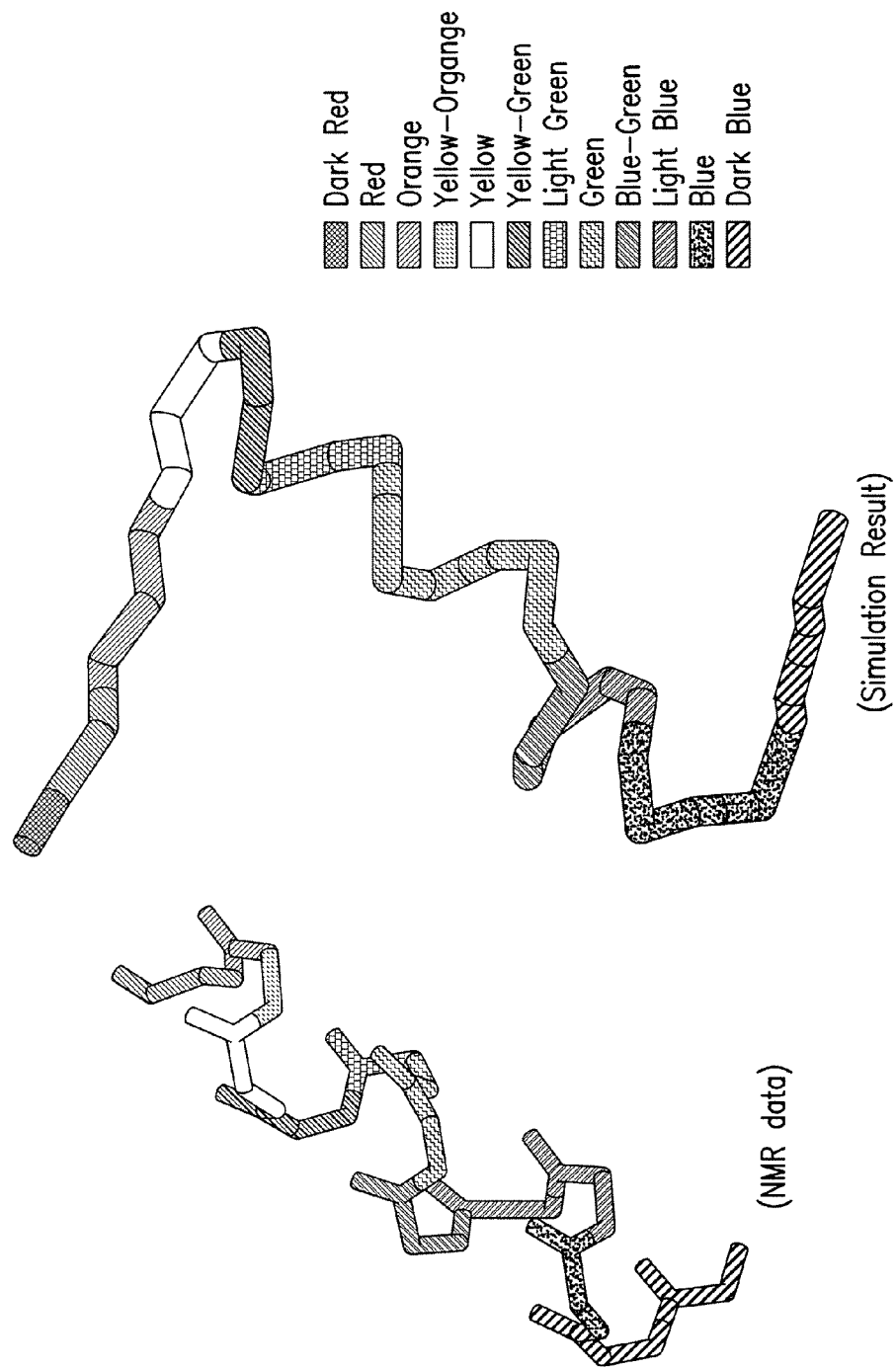
FIG. 11 is an illustrative diagram comparing the simulation-generated protein structure against experimental NMR data for the same.
Figure 12A:
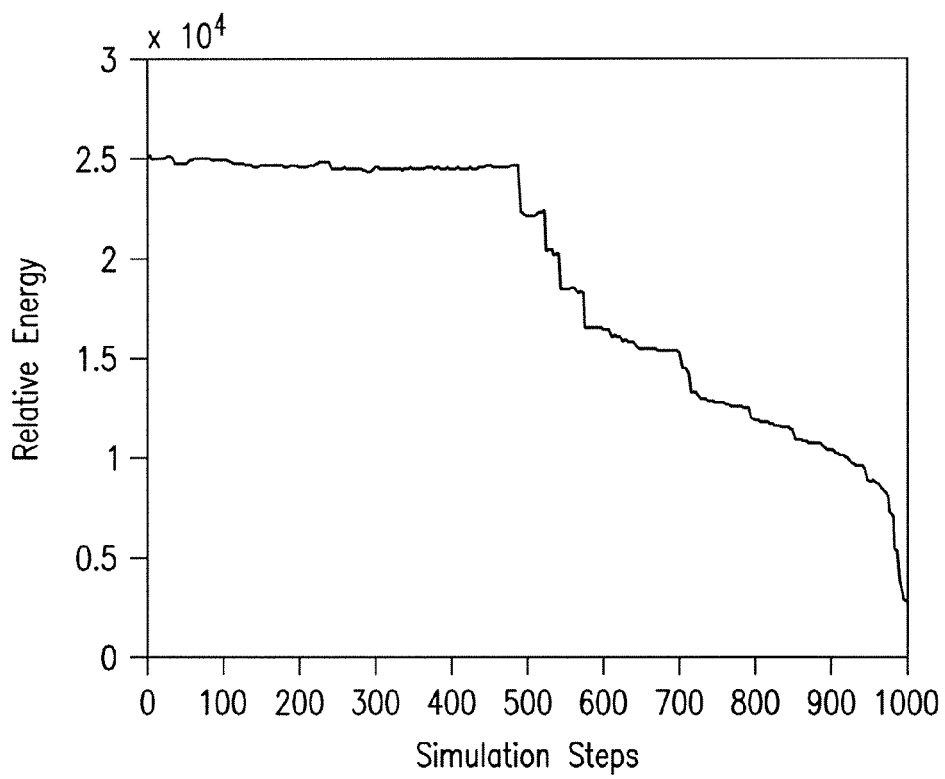
FIG. 12A is an illustrative diagram of simulation results using case D of FIG. 10 to determine the volume as a function of time in one embodiment of the invention.
Figure 12B:
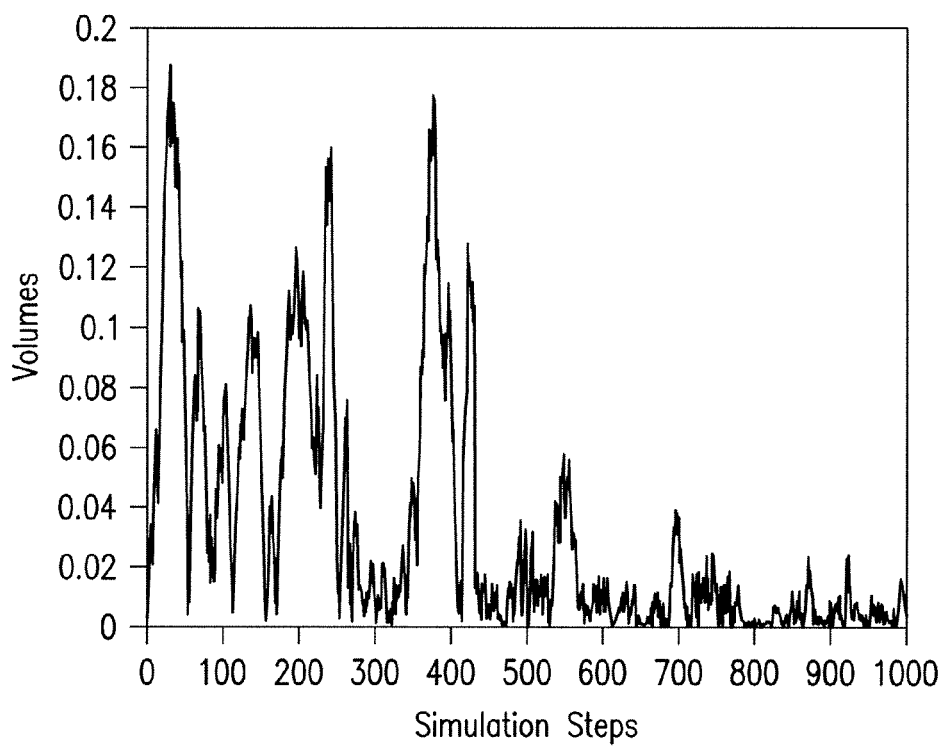
FIG. 12B is an illustrative diagram of simulation results using case D of FIG. 10 to determine the total energy as a function of time in one embodiment of the invention.

The hydrophobic force extension in the presence of an electric field is represented as double wells dependent on distance (one-half of the radius) between two charged particles, as shown in FIG. 8. Obstruction of the line-of-sight occurs when the mutual repulsion of several similarly charged residues prevent the rotation of all of the charged residues away from the line-of-sight region as shown in FIG. 9. If the space between two neighboring hydrophobic residues is sufficiently close such that the effective bubble and/or water/non-polar interface encasing each will wither directly touch and/or come into mutual contact with an equilibrium vapor bubble, the touching will generate a force that pulls the two residues closer together. This occurs via a set of rotations of the alpha carbon bonds between the two residues.

In the event a hydrophilic (polar) residue or other charged specie is attached to the protein in a position between the two residues, the energy stored in the polarized water surrounding it will seek to remain about the residue or charge specie. Accordingly, the residue or specie will experience a force tending to rotate it away from a vapor region or the hydrophobic residues encased in effective bubbles. This rotation can be inhibited by factors such as steric hindrance or electric fields created by other charged species.

Take, for example, a situation wherein two or more similarly charged residues interfere with each other as they attempt to rotate away from a vapor-filled region, thereby remaining surrounded by polarized water (or other media). Due to their proximity, when the residues rotate to the same side of the protein backbone chain, the distance between them will decrease. This distance change corresponds to a significant energy increase due to Coulomb repulsion. It is reasonable to expect that this energy is sufficiently large so as to overcome energy reductions made possible by hydrophobic residues coming close enough to reduce the water/non-polar and/or vapor interface.

It should be noted that two hydrophilic residues of opposite or nearly opposite charge will automatically rotate to the same side of the backbone chain so as to reduce the distance between them. The presence of two such residues between two hydrophobic residues would not inhibit extension of the non-polar/vapor interface necessary for the generation of hydrophobic force since the two can rotate as a unit. The electric field produced by two hydrophilic residues diminishes much faster than that of a single point charge. In some ideal cases it may be that two hydrophilic residues of opposite or nearly opposite charge have a sufficiently small electric field (and therefore small amount of surrounding polarized water/media) that the surrounding polarized water is stripped away, allowing the two hydrophilic residues to occupy a space within a vapor-filled region directly between two neighboring hydrophobic residues.

Computationally, the obstruction condition for the blocking the interaction of two neighboring hydrophobic residues by an number of hydrophilic and/or charted species is satisfied when $$\left|\sum_i q_i\right| = \sum_i |q_i| \tag{25}$$

where $q_i$ is the charge on i-th charged residues located in the region between the two hydrophobic residues. Under such condition, the intervening charged residues have the same sign of charges and therefore would be inhibited from moving to one side of the backbone chain to allow the formation of an effective bubble, such that the long-range hydrophobic force $h_2$ between the two residues, shown in FIG. 8, is inapplicable.

Physical consideration of the bubble extension of the hydrophobic force is a function of the actual residues involved, whether or not said residues are hydrophobically bound to other hydrophobic residues (thereby said double or triple hydrophobic residues can extend further for a given thermal energy, kT), and a function of environment (such as but not limited to temperature, ionic densities, pH, presence of surfactants, and the presence of other proteins, polypeptides, molecules, or atoms. Said force map representation of said bubble extension of the hydrophobic force can have multiple extensions predicated by said considerations.

Again we choose Ubiquitin to illustrate the effect of hydrophobic interactions in protein folding simulation. The initial state was a linear representation of the Ubiquitin backbone where the charge and degrees of hydrophobicity of each of the side chain amino acid residues are known (e.g., by using methods such as the comparison of heats of solution in polar and non-polar solvents, see Robert A. Copeland, *Methods for Protein Analysis, A Practical Guide to Laboratory Protocols*, Chapman & Hall, NY, 14 (1994)), and their values were assigned to appropriate locations on the protein backbone chain.

FIG. 10 shows the results of Ubiquitin simulations under various hydrophobic force parameters using a constant mobility. Case (A) shows the simulation result 1010 using only electrostatic driving forces. The simulation did not produce an alpha helix region. Case (B) shows is the simulation result 1020 using both electrostatic forces and hydrophobic forces, where only a short-range square well hydrophobic force in FIG. 8 is used. The protein structure obtained has unnatural and large loops that do not easily dissociate. Extending the operating range of hydrophobic force to 0.75 nm with a second shallower square well in FIG. 8 in case (C) enhances the probability that two nearly spaced hydrophobic residues experience a hydrophobic force sufficient to result in motion under the conditions of the simulation in the helix region as the second and third neighbor hydrophobic residues react strongly and early in the simulation prior to loop formation, which is evidenced by the observation in 1030 of a central counter loop 1035 formed by an alpha helix. Note, there may exist hydrophilic residues between said hydrophobic residues. However, unnatural hairpin loops form in a beta sheet region under this condition. Depicted at 1040 and 1060 is the result obtained in case (D) using the conditional line-of-sight charged residue consideration of equation 25. It is observed that beta sheet regions remain flat and alpha helix regions form loops with orientation consistent with a smooth unidirectional helix, which is consistent with experimental results obtained from NMR imaging at 1050 and 1070.

The average simulation time for producing the secondary structure is of the order of $10^{-5}$ s to $10^{-4}$ s and consumes about ten minutes of CPU time on a standard desktop computer. Note that the simulation time needed is dependent on the diffusion constant used, and more accurate determination of the diffusion constant would lead to a better approximation of the folding time. The calculated folding times are within the 8 ms time frame beyond which regions of Ubiquitin become inaccessible to the proton exchange mechanisms Briggs and Roder used to characterize folding times. See Martha S. Briggs and Heinrich Roder, *Proc. Nat. Acad. Sci.* 89, 2017-2023 (1992). Also the result 1040 case (D) in FIG. 10 is in agreement with the collapse characteristics described by Jacob et al. Jaby Jacob, Bryan Kranz, Robin S. Dothager, P. Thiyagarajan, and Tobin R. Sosnick, *J. Mol. Bio.* 338, 369-382 (2004). A further comparison of the simulation result to experimental data obtained from NMR imaging is shown in FIG. 11

FIGS. 12A and 12B show the time evolution of the RMS (root-mean-square) energy and volume, respectively, for the case where both the electrostatic and conditional hydrophobic extension forces were applied. The energy in this case was calculated by assuming an arbitrary initial energy and subtracting the work done, $F \cdot \theta \cdot r_0$, done in each time step where F is the force applied (the sum of hydrophobic, electrostatic, and thermal forces), θ is the calculated angle change, and $r_0$ is the average lever arm length of the protein.

At the onset of folding there are large forces along the line-of-sight between various charged locations and large hydrophobic forces particularly in the regions that will develop an alpha helix. However, the resolved forces in the direction of Ramachandran angle rotation are small. The nearly spaced residue hydrophobic interactions soon dominate the energy selection algorithm steps. The volume change and the energy released in the alpha helix formation are small as these involve a relatively small fraction of the protein atoms and because the distance over which the forces act are short. Because of the shape of the hydrophobic force map (FIG. 8) it is necessary to provide a halt after a fixed number of steps (typically ten time steps) and freeze the relative position of the hydrophobic near neighbor residues for a fixed time period so that the algorithm will proceed to sample through the next largest forces. After the initial incubation time the protein quickly collapses as the Ramachandran rotation axis come into favorable orientation with respect to the large electrostatic and hydrophobic torques.

At long times thermal fluctuations again dominate with small volume and energy changes. These will not damp out in a simulation involving real temperature and are considered to be representative of a real protein in a liquid water environment at room temperature. Nonetheless, the inclusion of the hydrogen bonding and other considerations consistent with tertiary structure would be expected to reduce the volume excursion but not necessarily the energy excursions.

Figure 13:
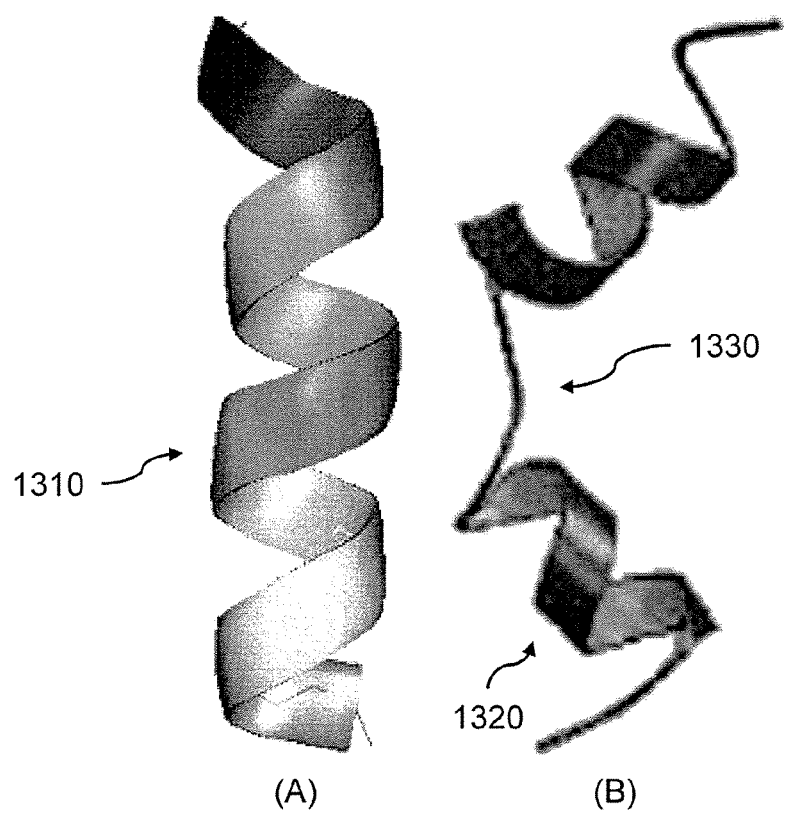
FIG. 13 is a diagram of the most accepted structure of the nAChR M2 protein 1310, and an alternate nAChR M2 structure 1320 (commonly though to exist at the onset of denaturizing) having an obvious kink 1330 in the central region of the alpha helix.

Referring to FIG. 13, the nAChR M2 α-helix region was modeled in order to demonstrate the ability of one embodiment of the invention to generate secondary structure. The M2 is one of a large number of alpha helix regions that line the ion channel in nAChR. Although it is known that the basic structure of M2 is an α-helix 1310, there is some debate as to whether a kink or super-coiled region 1330 of the alpha helix exists 1320 in the central region during the gating of ionic flow. See Law Richard J., Forrest, Lucy R., Ranatunga, Kishani M., Rocca, Paola La, Tieleman, Peter, and Sansom, Mart S. P., *Proteins: Structure, Function, and Genetics*, 39, 47-55 (2000).

Figure 14:
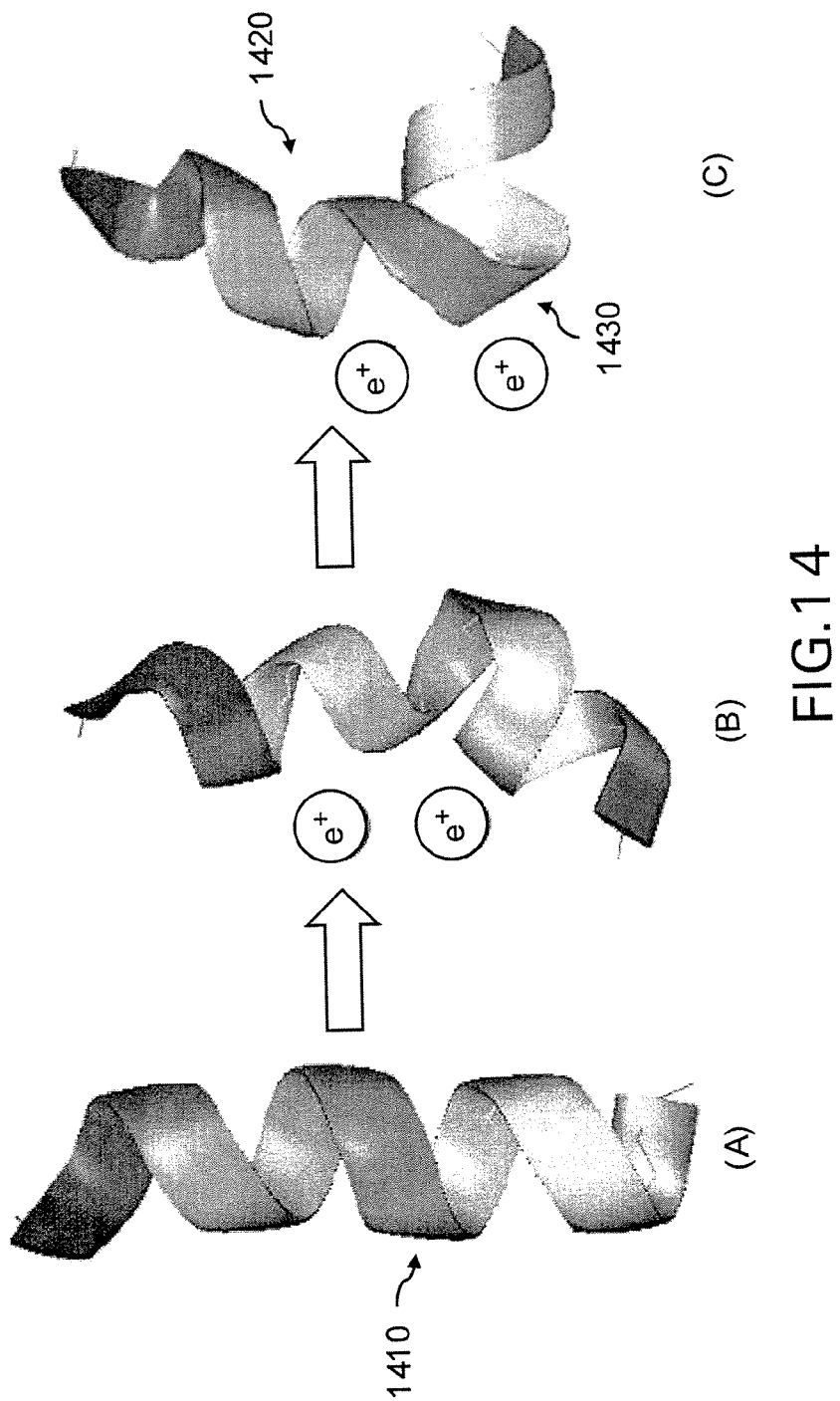
FIG. 14 is an illustrative diagram of the nAChR M2 protein structure generated using an embodiment of the invention incorporating a kinetic model wherein a positive two electron charge is placed near the central region of the alpha helix.

The algorithm was applied to the nAChR M2 structure. Under nominal residue charge states, an un-kinked structure 1410 similar to that of FIG. 13 was generated as shown in FIG. 14. However, if one or two charges are added to the central region, a kink 1430 appears as shown in 1420. The driving force for the kink formation can be easily understood in terms of the forgoing discussion of the model and its physical basis. Namely, the present of charge draws water a highly polar fluid with a correspondingly large dielectric constant, into the vapor filled alpha helix wherever the energy reduction presented by water filling a dielectric region is greater than the energy increase related to increased vapor-water and non-polar residue-water interface.

Environmental Effects

The simulation may be used to track the possible effects of various environmental changes. Environmental changes can have profound effects on protein secondary structure. For instance, illumination can, when the photon energy is sufficient, excite an electron of an atom in the protein and/or polypeptide and/or within water and/or other environmental media and/or species thereby changing the capacity of said atom with said excited electron to react with other elements or compounds within water, the protein and/or polypeptide. These reactions include the direct bonding of one element to another. This direct bonding can lead to local (to the bonding site(s)) changes in charge, hydrophobic character, and/or but not limited to flexibility of local bonds. Such changes can be tracked by the simulation.

Higher energy light (perhaps but not limited to photons with energy greater than ~2 eV) could lead to direct ionization of elements within water, materials within the environment, and/or the protein and/or polypeptide. This ionization leads directly to a change in the charged locations within the protein and/or polypeptide. The changes in-turn lead to changes in electromotive forces present in folding and folded proteins. Such changes can result in altered structure. Also ionization and the resultant charge change could lead to an alteration in local hydrophobic character thereby induces changes in hydrophobic interaction and structure.

The native structure of a polypeptide and/or protein in response to pH can be predicted using the simulation. pH can effect the concentration of ions in water and/or the media in which said polypeptide and/or protein under consideration is embedded. For example, pH can affect the presence of ions that turn effect the vapor/media (and/or water) and the hydrophobic residue/media (and/or water) interface. The interfacial energy in-turn has an effect on said surface tension of said interface. Some of the affects of pH are an increase in surface tension (promoting coalescence of bubbles and therefore increased hydrophobic force) while increased surface tension reduces the radius of equilibrium bubbles and increasing the energy needed to expand an existing bubble and/or envelop about a hydrophobic residue. This increase in energy corresponds to decreased probability of a given bubble displacement as well as a corresponding decrease in the distance at which the hydrophobic force can operate (to attract two hydrophobic residues toward one another). Also, pH can affect the probability of a solution hydrogen ion (and/or atom) attaching and/or bonding to the polypeptide and/or protein structure. Hydrogen bonding in-turn affects the charge structure of said polypeptide and/or protein thereby introducing a change that can be tracked by the simulation.

Importantly hydrogen ions and/or atoms can chemically bond to one location of the polypeptide and/or protein structure and then to a second location, thereby providing a new motive force drawing two said bonding locations together. Hydrogen bonding in-turn affects the charge structure of said polypeptide and/or protein thereby introducing a structural change that could be tracked by a modified version of the simulation.

The native structure of a polypeptide and/or protein in response to salts can also be predicted. Salts can effect the concentration of ions in water and/or the media in which said polypeptide and/or protein under consideration is embedded. For example, salt ions can in-turn effect the vapor/media (and/or water) and the hydrophobic residue/media (and/or water) interface. This interfacial energy in-turn has an effect on said surface tension of said interface, which can have the previously described effects.

The effects of charged species (pH related ions and/or salt related ions) can include a reduction of long-range interaction of protein charges on one another through the charge screening.

The native structure of a polypeptide and/or protein in response to non-polar, hydrophobic chaperons and/or small proteins existent in the environment and/or solution can also be predicted. Non-polar, hydrophobic chaperons and/or small proteins existent in the environment and/or solution can effect the concentration of effective bubbles present in the environment in which said polypeptide and/or protein under consideration is embedded. Since each small chaperons and/or small proteins are encased in an effective bubble the environment will be significantly changed. For example, one effect can be increased vapor/water interface area and vapor volume resulting in altered local electric field due to a change in the environmental dielectric constant and/or polarization. A change in the dielectric parameter would tend to increase the force arising from charge-charge interaction.

The increase in effective bubble density that includes bubble-encased non-polar, hydrophobic chaperons and/or small proteins may increase the range of the hydrophobic force through mechanisms described for natural equilibrium vapor bubbles. At very high concentrations of non-polar-hydrophobic chaperons and/or small proteins the force between neighboring hydrophobic residues on a particular protein and/or polypeptide under consideration may be reduced as a high concentration of chaperons and/or small proteins may displace sufficient amounts of water and/or other media so as to alter the surface energy throughout the local environment. Under conditions of reduced surface energy hydrophobic force and interaction is reduced. In extreme cases some structures stabilized and/or held together by hydrophobic interaction could denature and/or change structure.

Similarly, the native structure of a polypeptide and/or protein in response to polar, hydrophilic, and/or charged chaperons and/or small proteins existent in the environment and/or solution can be predicted. Polar, hydrophilic, and/or charged chaperons and/or small proteins existent in the environment and/or solution can affect local electric fields and/or nearby concentrations of effective bubbles and/or water (and/or other media)—hydrophobic (non-polar) residue interface in water (and/or the media) in which said polypeptide and/or protein under consideration is embedded since each such small chaperons and/or small protein induces a local electric field similar to that of an ion and/or point charge. At very high concentrations said chaperons and/or small proteins could markedly alter local protein structure and/or denature said protein structure through screening of interaction between charge-charge interaction and by decreasing the probability of vapor bubbles where ever the field of said chaperons and/or small proteins is sufficiently strong.

The native structure of a polypeptide and/or protein in response to metals can also be predicted. Metals can act as a concentration of ions in the water and/or the media in which said polypeptide and/or protein under consideration is embedded, producing effects similar to that described for ions and salts above. Also, metals (especially heavy metals) have electron clouds extending beyond 0.1 nm. A far-extending electron cloud can lead to charge screening resulting in modified charge-charge interaction within the protein and/or polypeptide under consideration. Metals and other elements can bond directly to the protein modifying local charge status and in-turn local hydrophobic character. These changes in local charge status can lead to altered charge-charge interaction and hydrophobic residue-hydrophobic residue interaction.

The effects on protein structure induced by species such as surfactants known to modify interfacial and/or water/vapor surface energies can be predicted using the simulation. The effect of mutations or viruses on protein and/or polypeptide structure can also be predicted using the simulation when and where they induce a change in local charge status, and/or local hydrophobic character, and/or the distance between neighboring hydrophobic residue pairs, and/or the screening charge-charge interaction, and/or the distance between charges, etc.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

We claim:

1. A method for determining an equilibrium structure of a protein in a predetermined environment, the protein having Ramachandran angles and a known denatured structure, comprising:
   (a) determining a maximum RMS volume of the known denatured structure of the protein;
   (b) calculating at least one force on the protein in its current structure in the predetermined environment;
   (c) determining, for each of the Ramachandran angles of the protein, at least one net torque resulting from the at least one force;
   (d) determining a greatest net torque from among the net torque(s) as determined in (c);
   (e) rotating at least one section of protein structure only on a side of a Ramachandran angle with the greatest net torque as determined in (d) to form a new structure;
   (f) determining a new RMS volume for the new structure;
   (g) determining the equilibrium structure of the protein by repeating (b) to (f) until the new RMS volume of the new protein structure at (f) is not less than the RMS volume of the structure of the protein in (a); and
   wherein, one or more of the features (a)-(g) are performed using a computer programmed to perform said one or more features.

2. The method of claim 1 wherein (b) to (e) are repeated until a fixed number of iterations have elapsed.

3. The method of claim 1 wherein the at least one force comprises the electrostatic force.

4. The method of claim 3 wherein the at least one force further comprises the thermal noise.

5. The method of claim 3 wherein the at least one force further comprises the hydrophobic force.

6. The method of claim 5 wherein determining the hydrophobic force includes determining a probability of formation of natural bubbles.

7. The method of claim 5 wherein the at least one force further comprises thermal noise.

8. The method of claim 1, wherein the equilibrium structure of the protein in a predetermined environment is known, and wherein (d) comprises:
   (i) determining a global energy change upon folding of the protein; and
   (ii) rotating at least one section of the protein structure only on a side of the Ramachandran angle with the greatest net torque as determined in (c) to form a new protein structure.

9. The method of claim 8 further comprising:
   (iii) calculating an approximate density using an average mobility; and
   (iv) determining a change in entropy from the approximate density.

10. The method of claim 9 further comprising:
    (v) modifying the mobility in (i) in an inverse relation to the change in entropy of (iv).

11. The method of claim 10 further comprising:
    (vi) repeating the rotation of (ii) using the modified mobility of (v).

* * * * *